United States Patent [19]

Imanishi et al.

[11] Patent Number: 5,726,705
[45] Date of Patent: Mar. 10, 1998

[54] SURFACE DEFECT INSPECTION APPARATUS

[75] Inventors: Masanori Imanishi, Tokyo; Kiyoshi Yoshida, Kanagawa; Teruo Asaeda, Tokyo; Yutaka Suzuki; Shigeru Chida, both of Kanagawa; Masami Watanabe, Yokohama, all of Japan

[73] Assignee: Nissan Motor Co., Ltd., Kanagawa, Japan

[21] Appl. No.: 770,571

[22] Filed: Dec. 19, 1996

[30] Foreign Application Priority Data

Dec. 28, 1995 [JP] Japan .................. 7-344054

[51] Int. Cl.⁶ ............................................. H04N 7/18
[52] U.S. Cl. ............... 348/92; 73/105; 356/237; 356/371; 382/108
[58] Field of Search ................. 348/128; 356/371, 356/237; 382/108; 73/105; H04N 7/18

[56] References Cited

U.S. PATENT DOCUMENTS 4,878,114  10/1989  Huynh ...................... 348/128
5,436,726  7/1995   Ventura et al. ............. 356/371
5,477,268  12/1995  Shimbara .................... 348/128
5,566,244  10/1996  Kato ........................ 382/108

FOREIGN PATENT DOCUMENTS 0491555   6/1992   European Pat. Off. .
64-38638  2/1989   Japan .

*Primary Examiner*—Howard W. Britton
*Attorney, Agent, or Firm*—Lowe, Price, LeBlanc & Becker

[57] ABSTRACT

A surface defect inspection apparatus a lighting unit shaped in an arched form laid across the path of movement of an object under inspection for illuminating its surface. A light diffusion sheet is located between the lighting unit and the path of movement of the object for forming a bright and dark light pattern on the surface of the object. A plurality of light sensors are arranged in an arched form laid across the path of movement of the object. Each of the light sensors produces an electrical signal in response to light of reflection from the surface of the object. The electrical signal is converted into an image including the bright and dark light pattern. This conversion is repeated to produce similar images in sequence for inspection of a defect which may exist on the surface of the object.

34 Claims, 22 Drawing Sheets

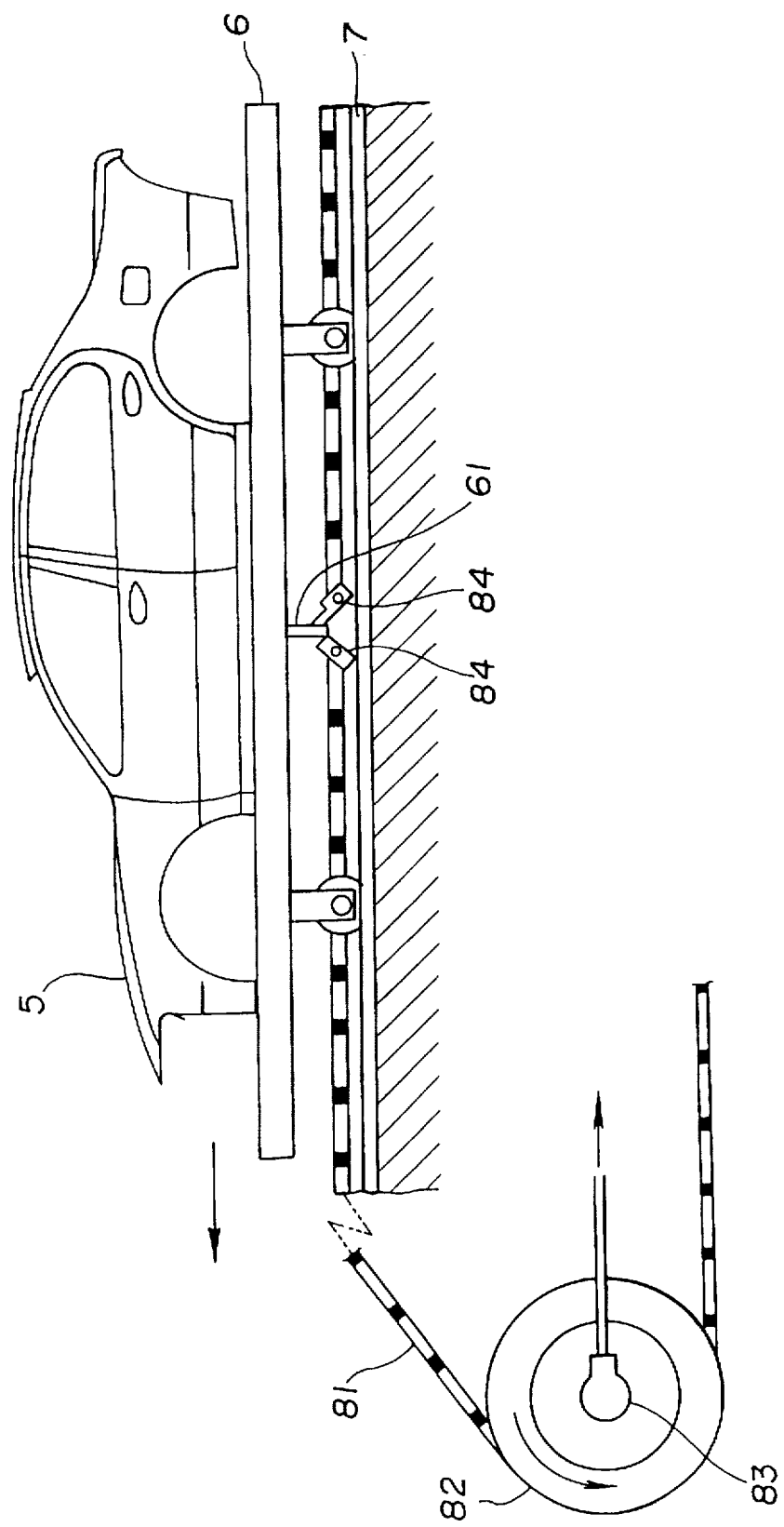

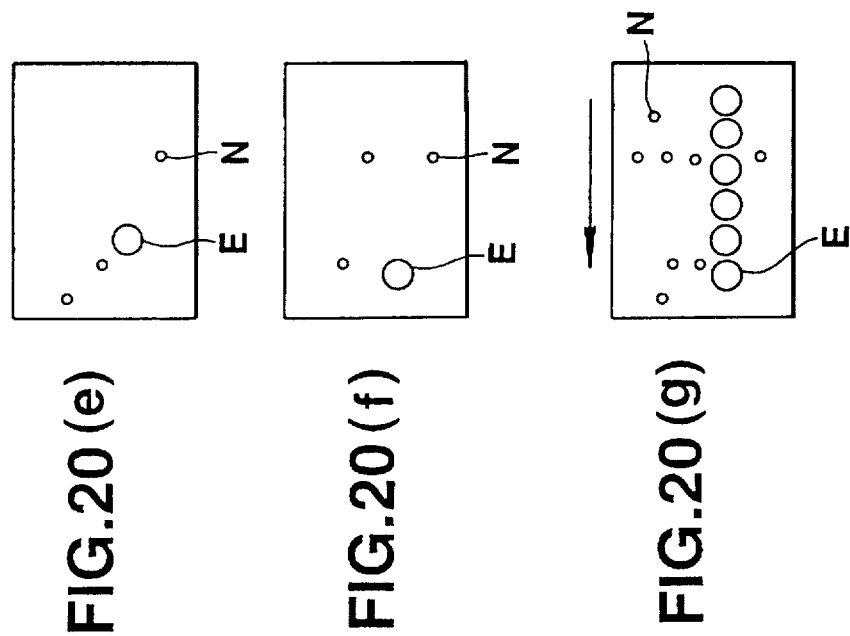
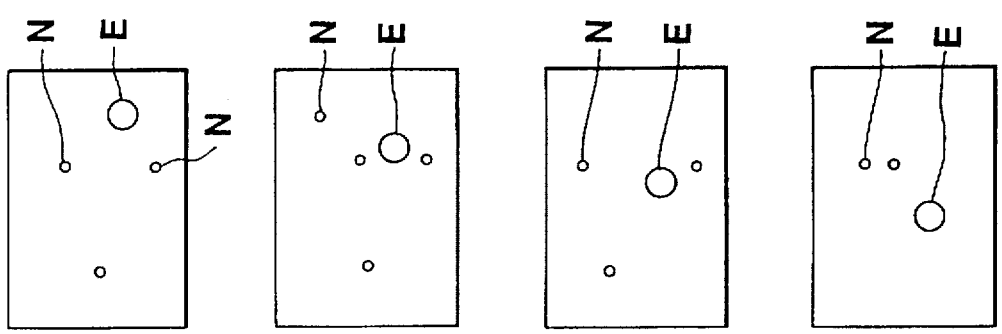
FIG.20(e)  FIG.20(f)  FIG.20(g)
FIG.20(a)  FIG.20(b)  FIG.20(c)  FIG.20(d)

SURFACE DEFECT INSPECTION APPARATUS

BACKGROUND OF THE INVENTION

This invention relates to an apparatus for inspecting defects or abnormalities on the surface of an object under inspection.

For example, Japanese Patent Kokai No. 64-38638 discloses a surface defect inspection apparatus arranged to produce images in sequence according to electrical signals fed from cameras directed to a moving light strap formed on the surface of an object under inspection. The images are edited into a total image for use in calculating the coordinates of a defect on the surface of the object. With such a conventional surface defect inspection apparatus, however, sophisticated controls are required to place the image at the image center of each of the cameras since the direction of reflection of the light strap changes according to the curvature of the surface of the object under inspection.

SUMMARY OF THE INVENTION

It is a main object of the invention to provide operable a surface defect inspection apparatus operable under simple controls to ensure accurate surface detect inspection.

There is provided, in accordance with the invention, an apparatus for inspecting a defect on a surface of an object under inspection. The surface defect inspection apparatus comprises means for moving the object along a path, a lighting unit shaped in an arched form laid across the path of movement of the object for illuminating the surface of the object, light pattern forming means located between the lighting unit and the path of movement of the object for forming a bright and dark light pattern on the surface of the object, a plurality of light sensors arranged in an arched form laid across the path of movement of the object, each of the light sensors producing an electrical signal in response to light of reflection from the surface of the object, a processing unit for processing the electrical signal fed thereto from each of the light sensors for producing an image including the bright and dark light pattern, and means for inspecting a defect on the surface of the object based on the images fed thereto from the processing unit.

BRIEF DESCRIPTION OF THE DRAWINGS

This invention will be described in greater detail by reference to the following description taken in connection with the accompanying drawings, in which:

FIG. 18 is a side view showing the conveyor on an enlarged scale;

FIGS. 20(a) to 20(g) shows images, similar to FIG. 19(c), produced in sequence;

FIG. 20(b) shows a total image into which the images of FIGS. 20(a) to 20(f) are edited;

DETAILED DESCRIPTION OF THE INVENTION

Figure 1:
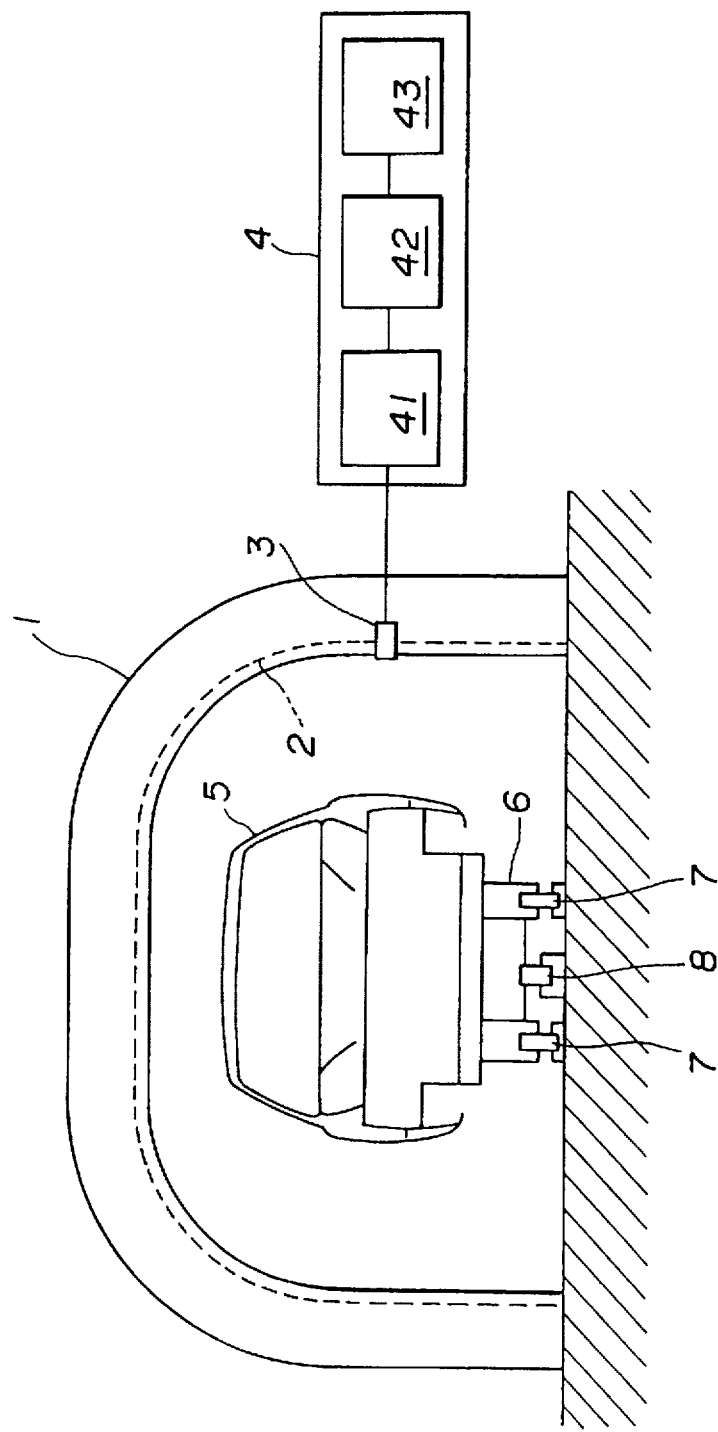
FIG. 1 is a schematic diagram showing one embodiment of a surface defect inspection apparatus made in accordance with the invention.
Figure 2:
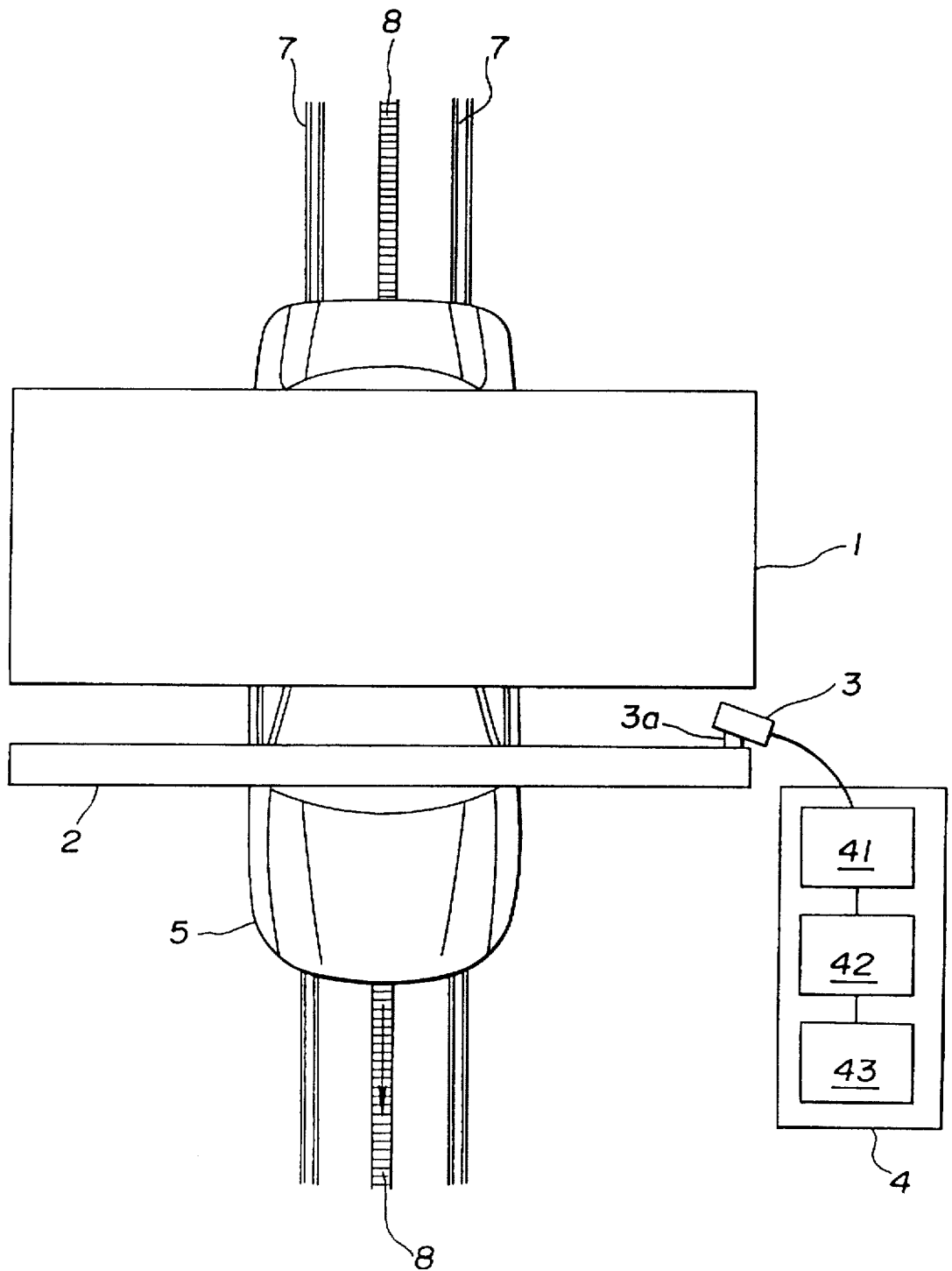
FIG. 2 is a plan view of the surface defect inspection apparatus of the invention.
Figure 3:
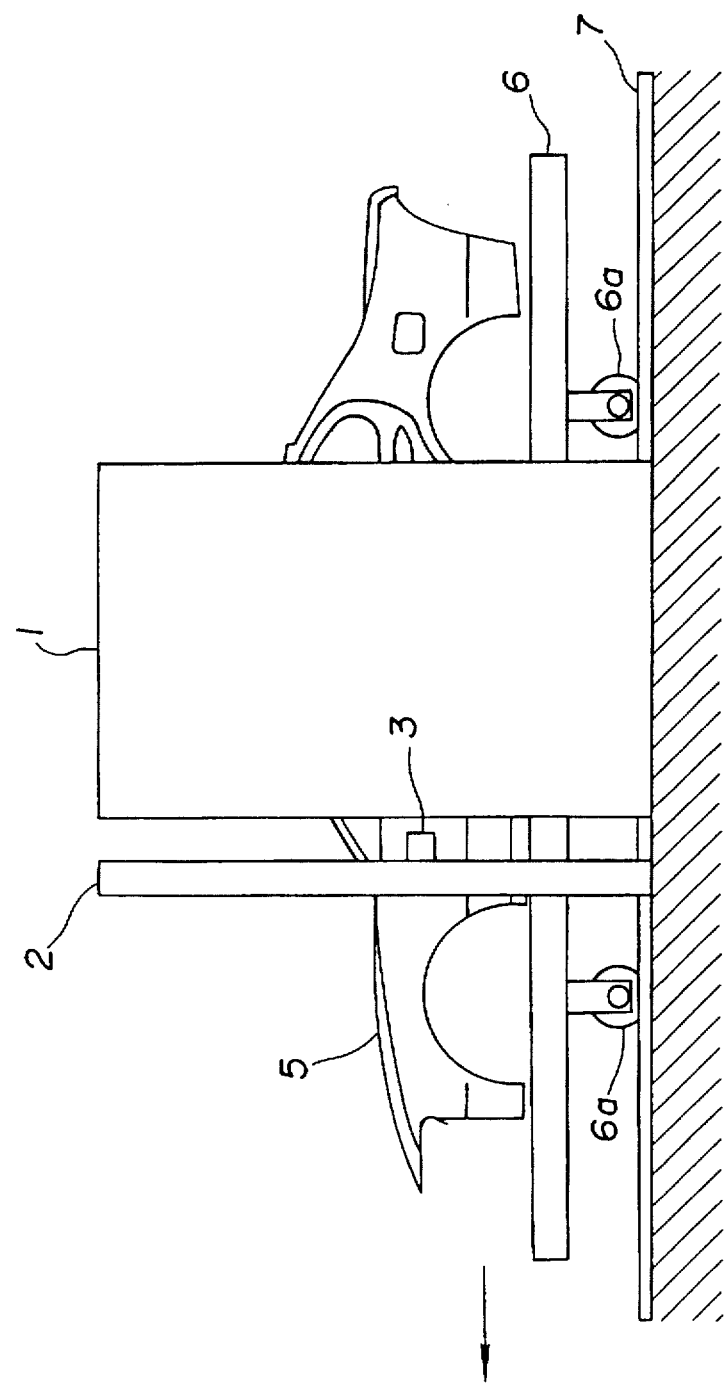
FIG. 3 is a side view of the surface defect inspection apparatus of the invention.

With reference to the drawings, wherein like numerals refer to like parts in the several views, and in particular to FIGS. 1, 2 and 3, there is shown a surface defect inspection apparatus embodying the invention. An object (in the illustrated case a vehicle body 5) under inspection is placed on a carriage 6 which is driven in the direction indicated by the arrow (FIG. 3) on a pair of rails 7 by a conveyor mechanism including a chain belt 8, a hook mechanism 84 (FIG. 18) and a drive wheel 82 (FIG. 18). The surface defect inspection apparatus includes a lighting unit 1, light sensors 3 and a processing unit 4. The lighting unit 1 is shaped in an arched form substantially in conformity of the front contour of the vehicle body 5 as viewed in the direction of movement of the vehicle body 5 and laid across the path of movement of the object for uniform illumination of the painted surface of the vehicle body 5. The lighting unit 1 may have a plurality of light sources positioned in an arched disposition substantially in conformity with the front contour of the vehicle body 5 or mounted at uniform intervals on a support frame shaped in a form substantially in conformity with the front contour of the vehicle body 5 so that all of the light sources are spaced substantially at the same distance from the painted surface of the vehicle body 5. This is effective to ensure uniform illumination of the painted surface of the vehicle body 5. This vertical frame is positioned in the direction normal to the direction of movement of the vehicle body 5. The light sensors 3, which may be in the form of CCD cameras, are arranged in an arched deposition substantially in conformity with the front contour of the vehicle body 5. The CCD cameras 3 may be mounted through respective adjustment tools 3a on a support frame 2 shaped in an arched form substantially in conformity with the front contour of the vehicle body 5 so that all of the CCD cameras 3 are spaced substantially at the same distance from the painted surface of the vehicle body 5. This is effective to ensure that all of the CCD cameras 3 have substantially the same visual field size. The support frame 2 is positioned in the direction normal to the direction of movement of the vehicle body 5. The adjustment tool 3a is designed to permit adjustment of the position and angle of the corresponding one of the CCD cameras 3 with respect to the painted surface of the vehicle body 5. The processing unit 4 includes an image enhancement section 41, a tracking section 42 and a host computer 43.

Figure 4:
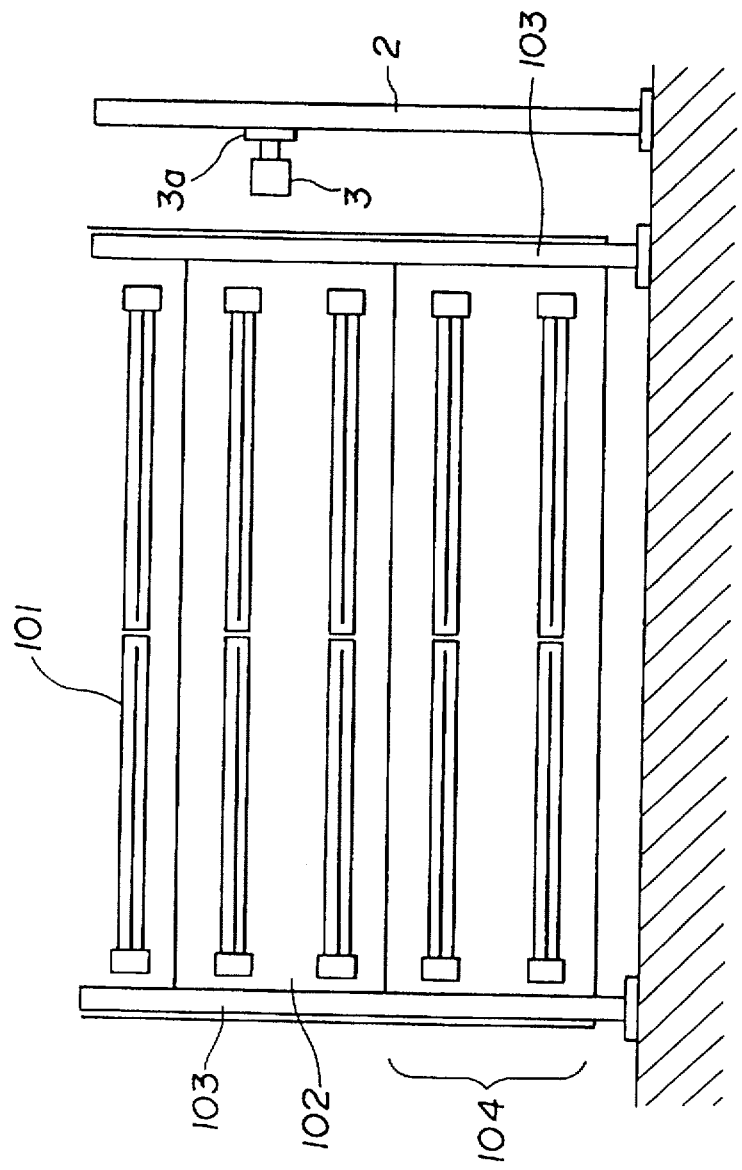
FIG. 4 is a fragmentary side view showing the lighting unit used in the surface defect inspection apparatus of the invention.
Figure 5:
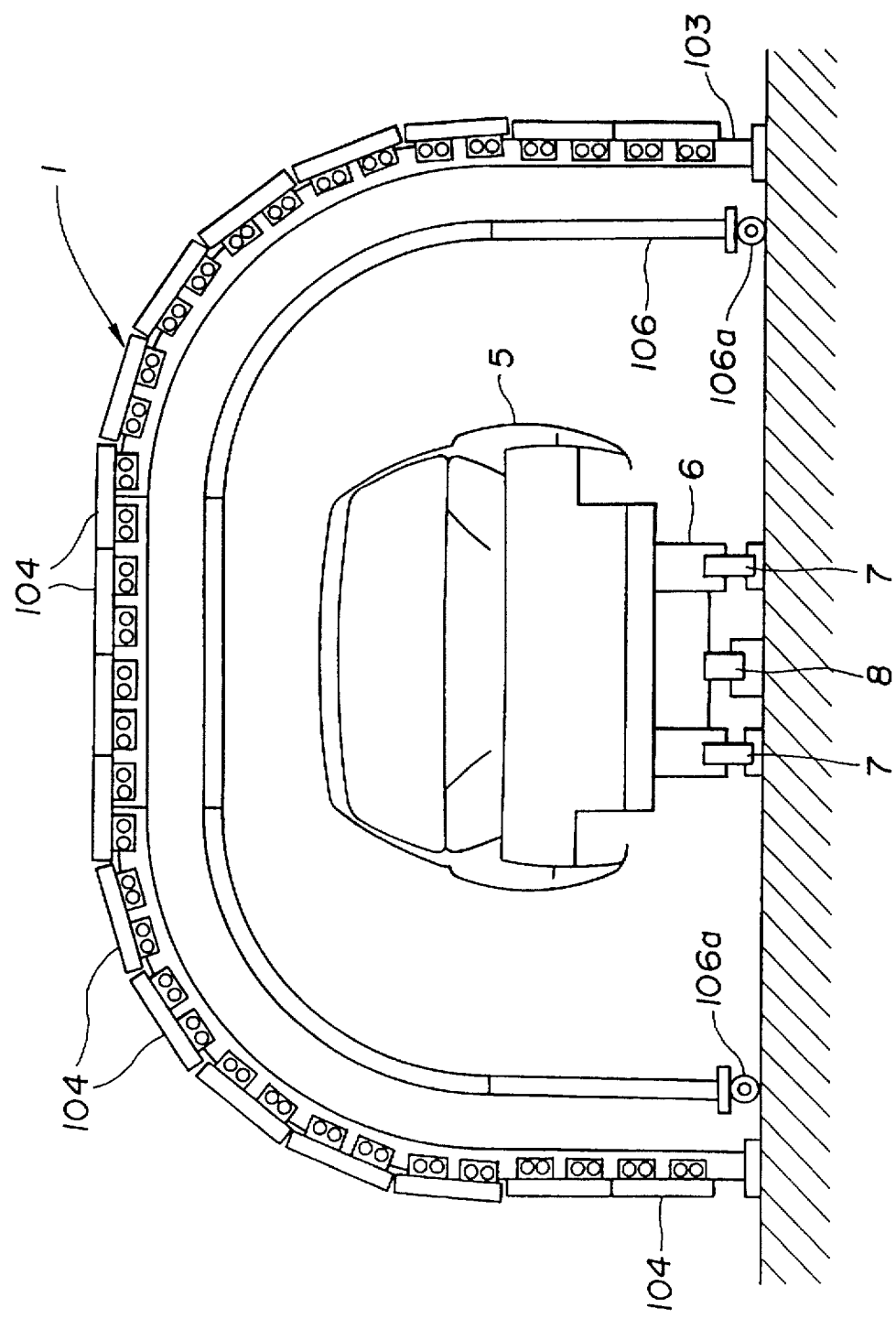
FIG. 5 is an elevational view showing the position of the lighting unit with respect to the vehicle body.
Figure 7:
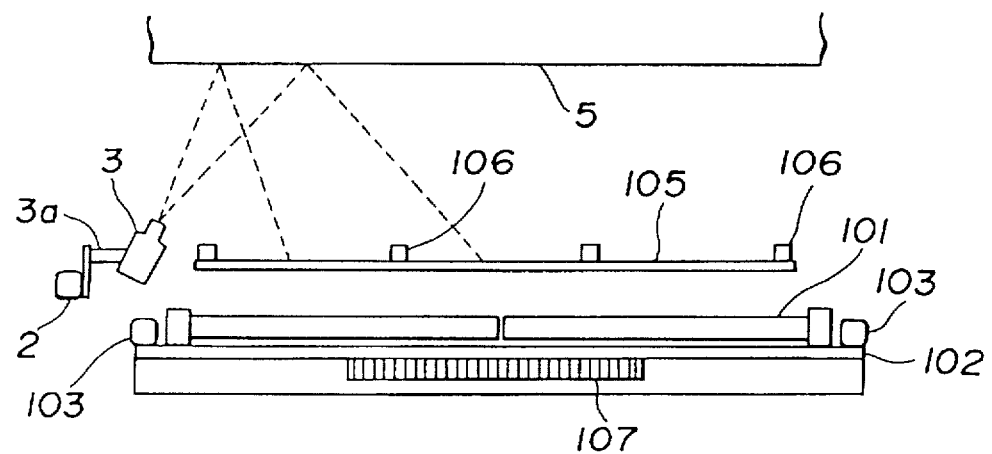
FIG. 7 is a plan view showing the positions of the lighting unit and camera with respect to the vehicle body.

Referring to FIGS. 4 and 5, there is shown a plurality of reflector 102 each of which is positioned in rear of a predetermined number of light sources 101. The reflector 102 has its surface treated for diffuse reflection of white rays so as to ensure uniform illumination of the light from the light sources 101 on the painted surface of the vehicle body 5 under inspection. In the illustrated case, four light sources 101, taken in the form of four U-shaped fluorescent lamps, are arranged in two rows in front of each of the reflectors 102. A power source 107 (FIG. 7) is mounted in rear of each of the reflectors 102 for supplying high-frequency power to drive the light sources 101. The light sources 101, the reflector 102 and the power source 107 are mounted as a unit on an arched strut 103, as best shown in FIG. 5.

Figure 6:
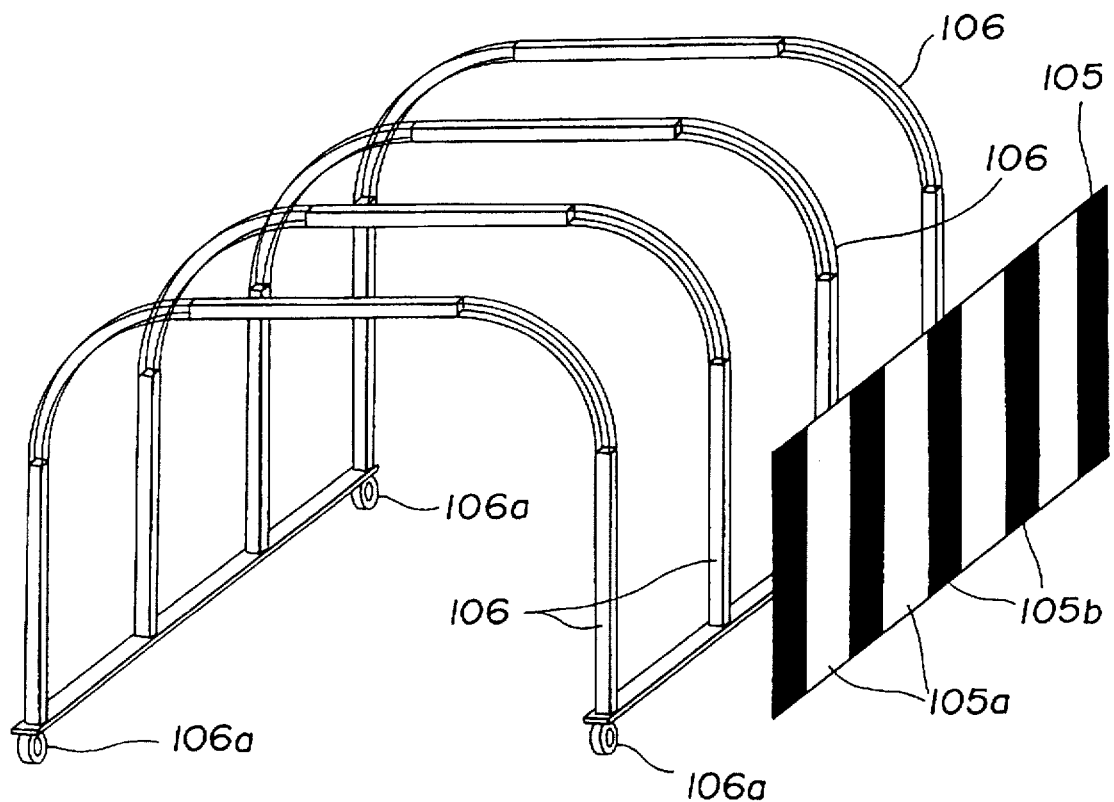
FIG. 6 is a perspective view showing the light diffusion sheet along with the sheet guide.
Figure 8:
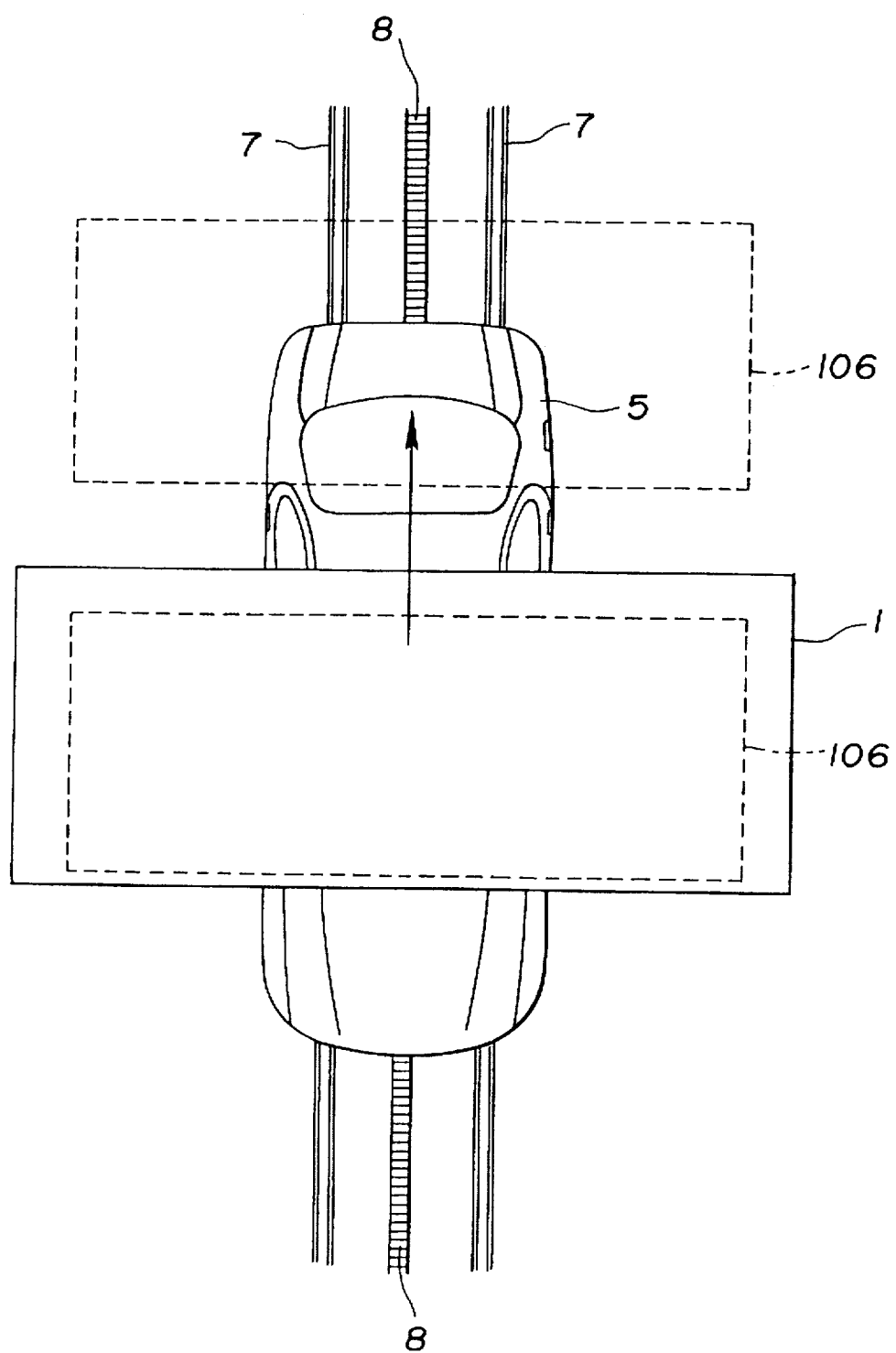
FIG. 8 is a plan view used in explaining the movement of the light diffusion sheet.

If the vehicle body 5 under inspection has a metallic coat on its surface, it would be preferable to minimum the influence of the bright material by positioning a light diffusion sheet between the lighting unit 1 and the vehicle body 5. The light diffusion sheet 105 is made of a flexible and transparent sheet 105a to permit easy deformation to a shape substantially in conformity with the front contour of the vehicle body 5. The light diffusion sheet 105 has frosted black masking tapes 105b stuck thereon so that transparent and frosted black portions 105a and 105b are arranged alternatively, as shown in FIG. 6, to form a bright and dark strip pattern. In order to eliminate the tendency of the light diffusion sheet 105 to produce wrinkles thereon, causing shade or uneven illumination on the painted surface of the vehicle body 5, the light diffusion sheet 105 may spread on a sheet guide 106 having a front shape substantially in conformity with the front contour of the vehicle body 5. The sheet guide 106 is coated with a frosted black paint. The distance of the struts 103 is determined in such a manner that the frosted black masking tapes 105b overlap the struts 103. The light diffusion sheet 105 is fixed to the sheet guide 106 at the struts 103 with the use of frosted black bolts, nuts and washers. The sheet guide 106 has casters 106a for forward and rearward movement with respect to the vehicle body 5. This is effective to move the sheet guide 106 to a place for an easy exchange of a broken light source 101, as shown in FIG. 8.

Figure 9:
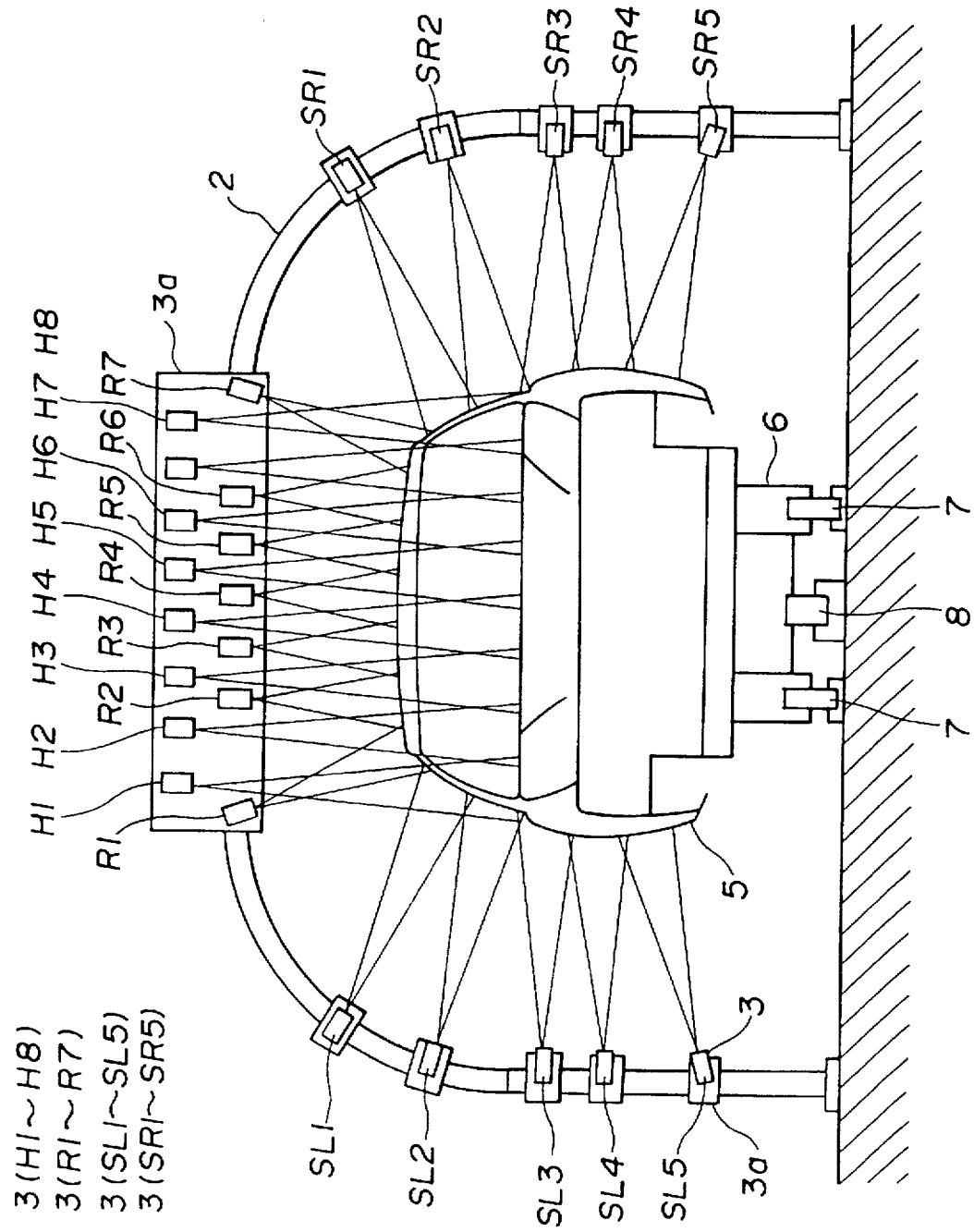
FIG. 9 is an elevational view showing the positions of the cameras with respect to the vehicle body.
Figure 10:
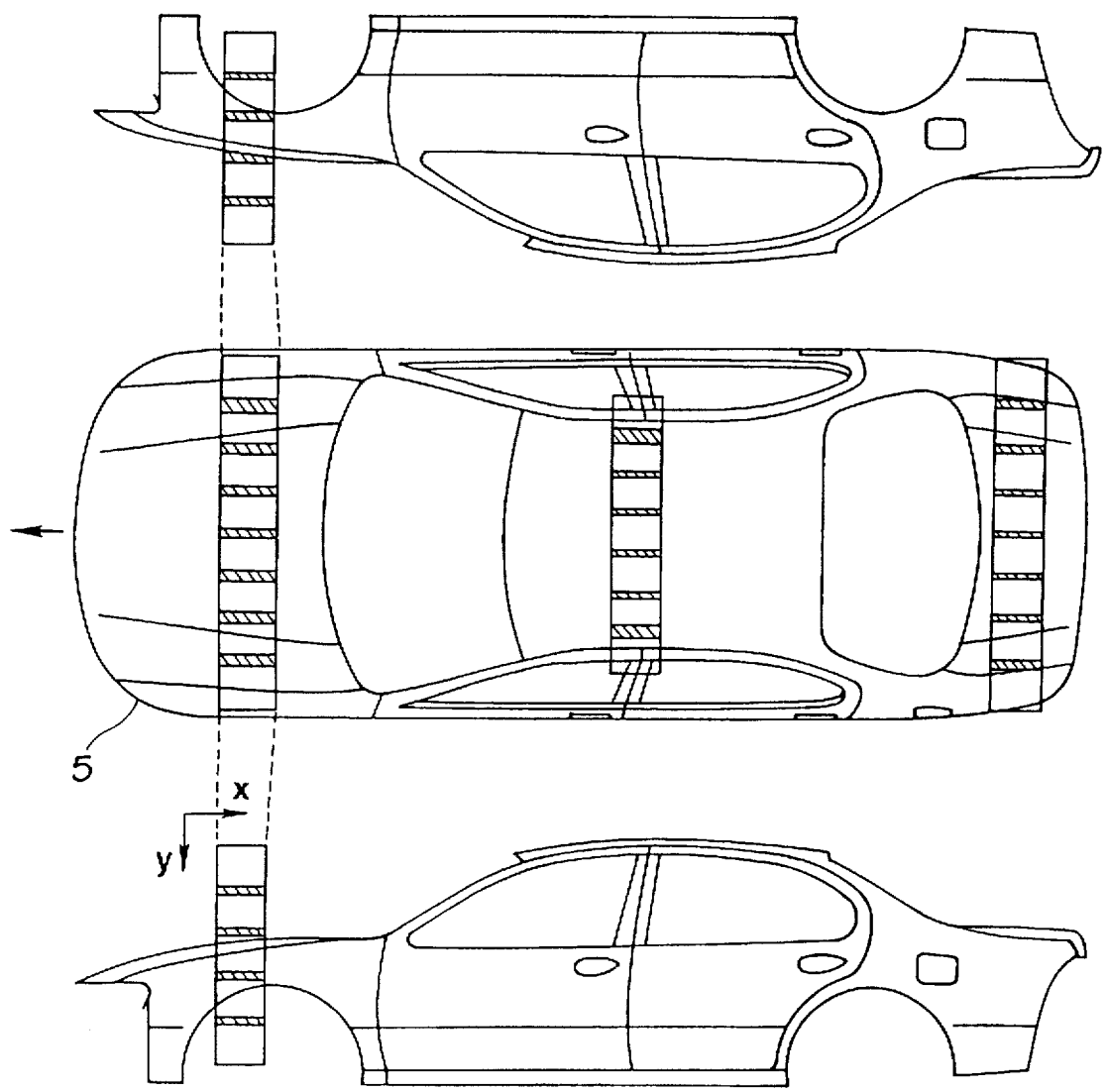
FIG. 10 is a vehicle body development used in explaining the visual fields of the cameras.

Referring to FIG. 9, the support frame 2 has a shape substantially in conformity with the front contour of the vehicle body 5 so that all of the CCD cameras 3 are positioned substantially at the same distance away from the painted surface of the vehicle body 5 and they have substantially the same visual field size. The adjustment tool 3a is used for the fine adjustment of the distance and direction of the corresponding one of the CCD cameras 3 according to the configuration of the vehicle body 5 under inspection. If a great degree of adjustment is required over the capacity of the adjustment tool 3a, for example, for an inspection of a defect on a stepped surface expanding between the hood (bonnet) and roof of the vehicle body 5, the lens focal length may be changed to change the size of the visual field of each of the CCD cameras 3. The CCD cameras 3 are adjusted in such a manner that the visual fields of the adjacent CCD cameras 3 overlap each other in a strap-shaped area having a width greater than a predetermined value, as shown in FIG. 10. A surface having a great step, such as a surface expanding between the hood and roof of the vehicle body 5, cannot be inspected by the same CCD camera 3. Such a surface defect inspection may be made with the selective use of two groups of CCD cameras 3, as shown in FIG. 9, where a first group of CCD camera (3)H1 to H8 is used for inspection of a defect on the hood of the vehicle body 5 and a second group of CCD cameras (3) R1 to R7 is used for inspection of a defect on the roof of the vehicle body. The selection of the two groups of CCD cameras 3 may be changed at a position, indicated by the character C of FIG. 21, where no inspection is required, for example, at a position of the front or rear window of the vehicle. In this case, the CCD cameras (3)R1 to R7 used for defect inspection on the roof of the vehicle body 5 have a strap-shaped total visual field, as shown in FIG. 10, like the CCD cameras (3) SL1 to SL5 used for defect inspection on the left side surface of the vehicle body 5, the CCD cameras (3) SR1 to SR5 used for defect inspection on the right side surface of the vehicle body 5 and the CCD cameras (3)H1 to H8 used for defect inspection on the hood of the vehicle body 5. The visual fields of these CCD cameras 3 are indicated by the hatched areas of FIG. 10. The required number of the CCD cameras 3 increases as the area where the visual fields overlap each other increases. It is, therefore, preferable to determine the overlapped area after determining the image resolution, that is, the size of the visual field of each of the CCD cameras 3 according to the minimum size of a defect to be inspected and determining the number of the CCD cameras 3 required for defect inspection over the whole area of the vehicle body 5 under inspection according to the visual field size.

Referring to FIG. 18, there is shown an inspection line used in the invention. The vehicle body 5 is carried on a carriage 6 transported by the conveyor mechanism 8 which includes a chain belt 81 loop around a drive wheel 82. A pulse generator 83 is associated with the drive wheel 82 for producing information on the degree of rotation of the drive wheel 82. The hooks 84 engage with the pawl 61 fixed on the lower surface of the carriage 6 so that the chain belt 81 is driven to move the vehicle body 5 when the drive wheel 82 rotates in the direction indicated by the arrow. If the engagement of the hooks 84 with the pawl 81 is loose, the amount of movement of the chain belt 81 will not be in coincidence with the amount of movement of the carriage 6 on which the vehicle body 5 is placed. As a result, the calculation of the amount of movement of the vehicle body 5, which is made based on the information on the degree of rotation of the drive wheel 82 fed from the pulse generator 83, becomes erroneous to reduce the inspection accuracy. According to the invention, the front and rear sides of the pawl 61 is retained in contact with the respective hooks 84. It is also possible to bring the speed of movement of the vehicle body 5 closer to the speed of movement of the conveyor 8 by adjusting the chain belt 81 in a manner to have no slack thereon. The conveyor 8 and the rails 7 may be inclined upward in the direction of movement of the vehicle body 5 to hold the pawl 61 in contact with the hooks 84 by the weight of the vehicle body 5. Such a speed adjuster means is not limited in any way to these examples.

The vehicle body 5, which is carried on the carriage 6 moving at the same speed as the conveyor 8 by the function of the speed adjuster means, moves smoothly at a slow speed with no vibration along the rails 7 within the support frame 2. At the same time, the processing unit 4 performs an automatic inspection for defects or abnormalities on the painted surface of the vehicle body 5 under inspection.

Figure 19A:
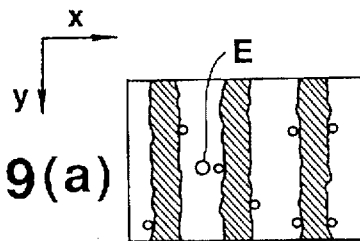
FIG. 19(a) shows an image produced from the camera.
Figure 19B:
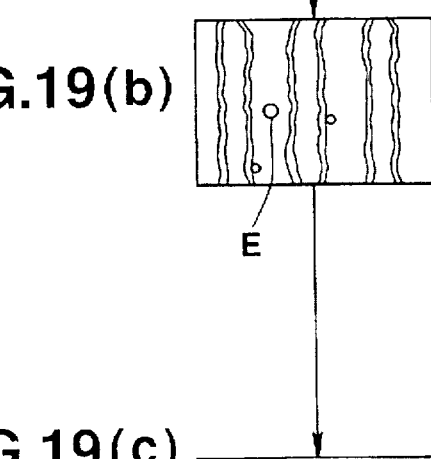
FIG. 19(b) shows an enhanced image.
Figure 19C:
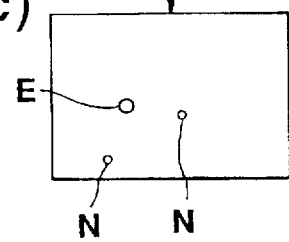
FIG. 19(c) shows an image having small isolated points extracted from the image of FIG. 19(b)
Figure 19D:
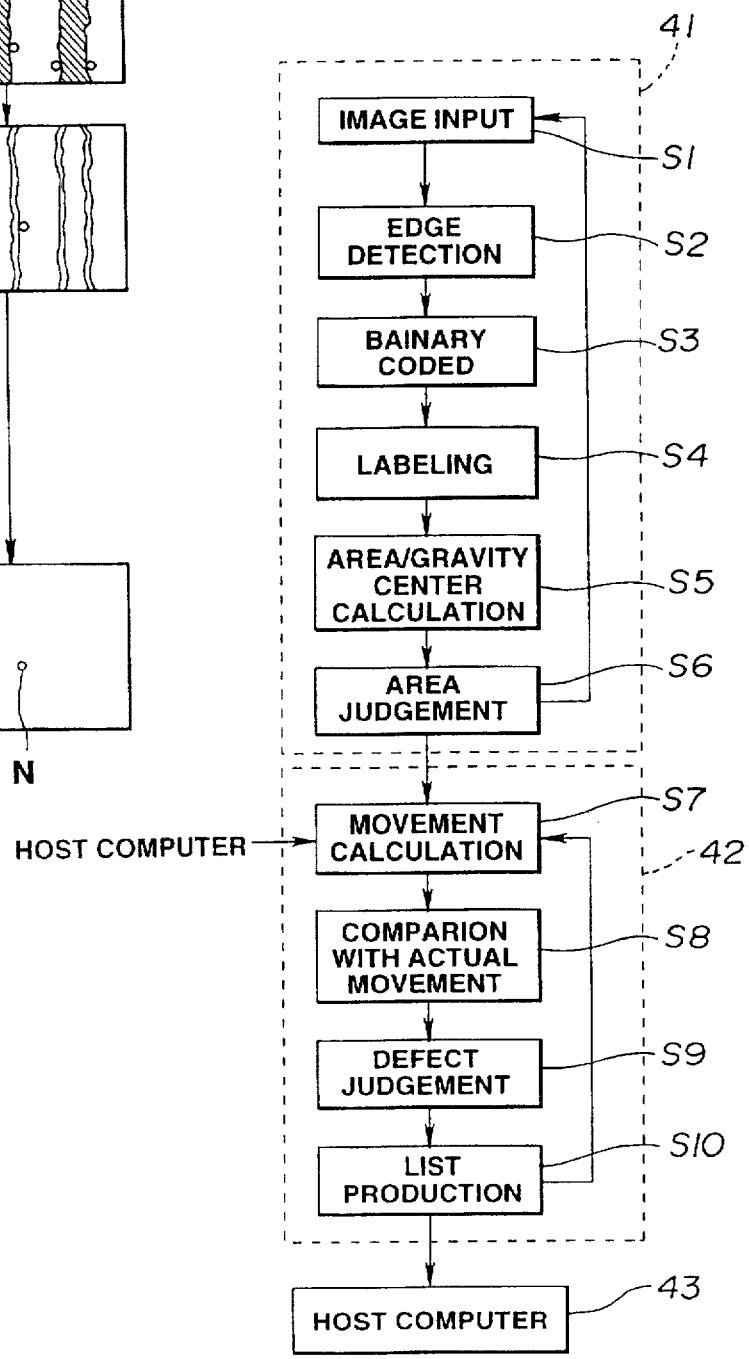
FIG. 19(d) is a flow diagram showing a sequence of steps performed in the processing unit.

FIG. 19(d) is a flow diagram showing a sequence of steps made in the processing unit 4. FIG. 19(a) shows an image produced from a CCD camera 3 focused to the painted surface of the vehicle body 5 having a bright and dark strip light pattern formed thereon by the function of the light diffusion sheet 105. In the step S1, the image enhancement section 41 receives the image (FIG. 19(a)) from the CCD camera 3. As can be seen from FIG. 19(a), this input image has dark image areas corresponding to the dark strips of the light diffusion sheet 105 and a bright image area produced because of irregular reflection on a rough portion (defect) of the surface of the vehicle body 5 under inspection. In the step S2, the image enhancement section 41 differentiates the image for edge detection. Upon completion of the edge detection, the image enhancement section 41 compares the light intensity of each of the pixels of the differentiated image with a predetermined threshold value to produce a binary coded image in the step S3. FIG. 19(b) shows the binary coded image. The binary coded image has a white image area for a surface portion having its brightness changed, that is, an image area having high spatial frequencies and a black image area for the other surface portions. Then, the binary coded image, as shown in FIG. 19(b), is labeled (numbered) in the step S4 and the area and gravity center of the image are calculated in the step S5. The image enhancement section 41 utilizes the fact that the defect is indicated by an isolated point E having a small image area as can be seen from the binary coded image of FIG. 19(b) to extract small image areas by comparing the calculated areas with a predetermined value in the step S6. FIG. 19(c) shows an image having extracted isolated points E and N. The points N indicate small rough portions on the coated surface. Such small rough portions, which are called as orange-peel and not defective, may be extracted along with the defect, as shown in FIG. 19(c). The small rough portions N are referred hereinafter to as noises N.

Upon completion of the extraction of the small image points E and N, the tracking section 42 extracts the defect E from the image of FIG. 19(c). The principle of the defect extracting operation of the tracking section 42 is as follows: It is now assumed that a predetermined number of enhanced images, as shown in FIGS. 20(a) to 20(f), produced in sequence from the image enhancement section 41 are superimposed into a superimposed image, as shown in FIG. 20(g). Since the lighting unit 1 and the CCD cameras 3 are fixed, the defect E, which may exist on the painted surface of the vehicle body 5, will appear as small image areas arranged in the same direction on the superimposed image of FIG. 20(g). On the other hand, the noises N are produced at random regardless of the movement of the vehicle body 5. Therefore, it may be considered that a small image area E, which changes its position substantially in the same direction as the direction of movement of the vehicle body 5 and substantially at the same speed as the speed corresponding to the speed of movement of the vehicle body 5, indicates the defect on the printed surface of the vehicle body 5. If the CCD camera 3 has a visual field directed in parallel with the direction of movement of the vehicle body 5, the defect indicative small image areas E will be arranged in a vertical or horizontal direction on the superimposed image. In this embodiment, the CCD cameras 3 are fixed in such a direction that the defect indicative small image areas E is arranged in the direction parallel to the horizontal direction indicated by the arrow of FIG. 20(g).

The tracking section 42 is arranged to repetitively process two images produced in sequence from the image enhancement section 41. First of all, the tracking section 42 calculates the first y-coordinate of the gravity center of the white small image area on the precedent one of the two images and also the second y-coordinate of the gravity center of the white small image area on the subsequent image. The calculated first and second y-cordinates are compared. If the first and second y-coordinates are substantially the same, it means that a great possibility exists that these white small image areas indicate a defect E on the painted surface of the vehicle body 5 since the white small images areas E appear as moving in the horizontal direction on the two images and the tracking section 42 calculates the first x-coordinate of the gravity center of the white small image area on the precedent one of the two images and also the second x-coordinate of the gravity center of the white small image area on the subsequent image. The calculated first and second x-cordinates are compared in the step S7. The difference between the calculated first and second x-coordinates corresponds to the number of pixels existing between the positions of the white small image areas E and thus to the amount of movement of the defect E on the painted surface of the vehicle body 5. The sign of the calculated difference corresponds to the direction of movement of the defect E. In the step S8, the calculated pixel number is compared with the actual pixel number corresponding to the actual amount of movement of the vehicle body 5. If the difference calculated in the step S8 is within a predetermined range, it means that a much greater possibility would exist that the white small image areas indicate a defect E on the painted surface of the vehicle body 5 and the calculated coordinates (x, y) of the gravity center of the white small image area on the subsequent image are stored into the computer memory. The above sequence of steps is repeated. When the number of the coordinates (x, y) stored in the computer memory for one white small image area exceeds a predetermined value, it is judged in the step S9 that a defect exists on the painted surface of the vehicle body 5 at a position corresponding to the white small image area. In the step S10, the coordinate of the gravity center of the white small image area and the area of the white small image area are written on a defect list. The trucking means 42 repeats the above sequence of steps as long as the vehicle body 5 is in the visual field of the camera 3. After the vehicle body 5 moves out of the visual field of the camera 3, the defect list is transferred to the host computer 43.

The actual pixel number X is calculated from Equation (1)

$$X = (t \times v \times L)/A \qquad (1)$$

where t is the time interval at which the tracking section 42 receives the two images, v is the speed of movement of the vehicle body, L is the image size, and A is the size of the visual field of the camera 3. The time interval t, for example, 0.1 seconds, corresponds to the time required for the image enhancement section 41 to convert the image transferred thereto from the camera 3 into an enhanced image. The time interval t may be obtained by measuring the intervals of time at which the trucking section 42 receives two images from the image enhancement section 41. The host computer 43 receives the pulses from the pulse generator 83 and calculates the speed v of movement of the vehicle body 5 based on the speed of rotation of the drive wheel 82. The speed v, for example 100 mm/s, is transferred to the trucking section 42. The image size L corresponds to the number of pixels arranged on the image in the same direction as the direction of movement of the vehicle body 5. Assuming now that the image has a 512×480 array of pixels and the vehicle body 5 moves in the x direction, the image size L is 512. The camera visual field size A is the size of the visual field of the camera 3 in the same direction as the direction of movement of the vehicle body. Assuming now that the visual field (FIG. 10) is a rectangular area of 120×100 mm and the vehicle body 5 moves in the x direction, the camera visual field size A is 120 mm.

In this embodiment, the time interval t corresponds to the time required for the image enhancement section 41 to produce one enhanced image. If the vehicle body 5 moves at such a high speed as to pass the visual field of the CCD camera 3 in a time shorter than the time t, the tracking process will become impossible since the same defect does not appear twice or more on the images produced in sequence from the CCD camera 3. Thus, the time interval t, the speed v and the visual field size A should be set in such a manner that the same defect can appear at least twice on the images produced in sequence from the CCD camera. It is possible to facilitate required adjustments and calculations by executing the image enhancement process at uniform intervals of time since the time interval t is held constant.

At the last stage of the surface defect inspection made in the processing unit 4 for one vehicle body 5, a mark (for example, ●) is put on a body on the development of the vehicle body 5 at a position corresponding to each of the defects found on the vehicle body surface based on the surface defect inspection result. For this purpose, the processing unit 4 includes an inspection start/end detecting section and a movement measuring section. The inspection start/end detecting section monitors the movement of the vehicle body 5 and detects the time at which the surface defect inspection is initiated and the time at which the surface defect inspection is terminated. For example, the inspection start/end detecting section may be taken in the form of a transparent photoelectric switch mounted in a direction normal to the direction of movement of the vehicle body 5, at such a height that the front and rear ends of the vehicle body 5 intercept the light beam to the photoelectric switch and at such a position that the vehicle body 5 can intercept the photoelectric switch just before the front end of the vehicle body 5 comes into the visual field of the CCD camera 3. If the position of the carriage 6 with respect to the vehicle body 5 is known, the photoelectric switch may be positioned according to the position of the carriage 6. Alternatively, the times at which the surface defect inspection is initiated and terminated may be detected based on the difference between the brightness on an image produced when the vehicle body 5 is within the visual field of the CCD camera 3 and the brightness on a background image produced in the absence of the vehicle body 5 within the visual field of the CCD camera 3.

The movement measuring section measures the amount of movement of the vehicle body 5 with respect to a point at which the surface defect inspection is initiated. This point is detected by the inspection start/end detecting section. In this embodiment, the amount of movement of the vehicle body 5 is calculated based on the degree of rotation of the drive wheel 82 indicated by the electrical pulses fed from the pulse generator 83 and the time related information indicated by the clock pulses fed from the host computer 43. Since the processing section 4 can always grasp the position of the painted surface of the vehicle body 5 to be inspected and calculate the position of the defect E on the painted surface of the vehicle body 5 detected by the tracking section 42, the host computer 43 can read the defect information from the defect list stored in the computer memory. The defect information includes the area of the white small image area E corresponding to the defect on the painted surface of the vehicle body 5, the coordinates of the gravity center of the white small image area E and the position of the defect on the painted surface of the vehicle body 5.

Figure 21:
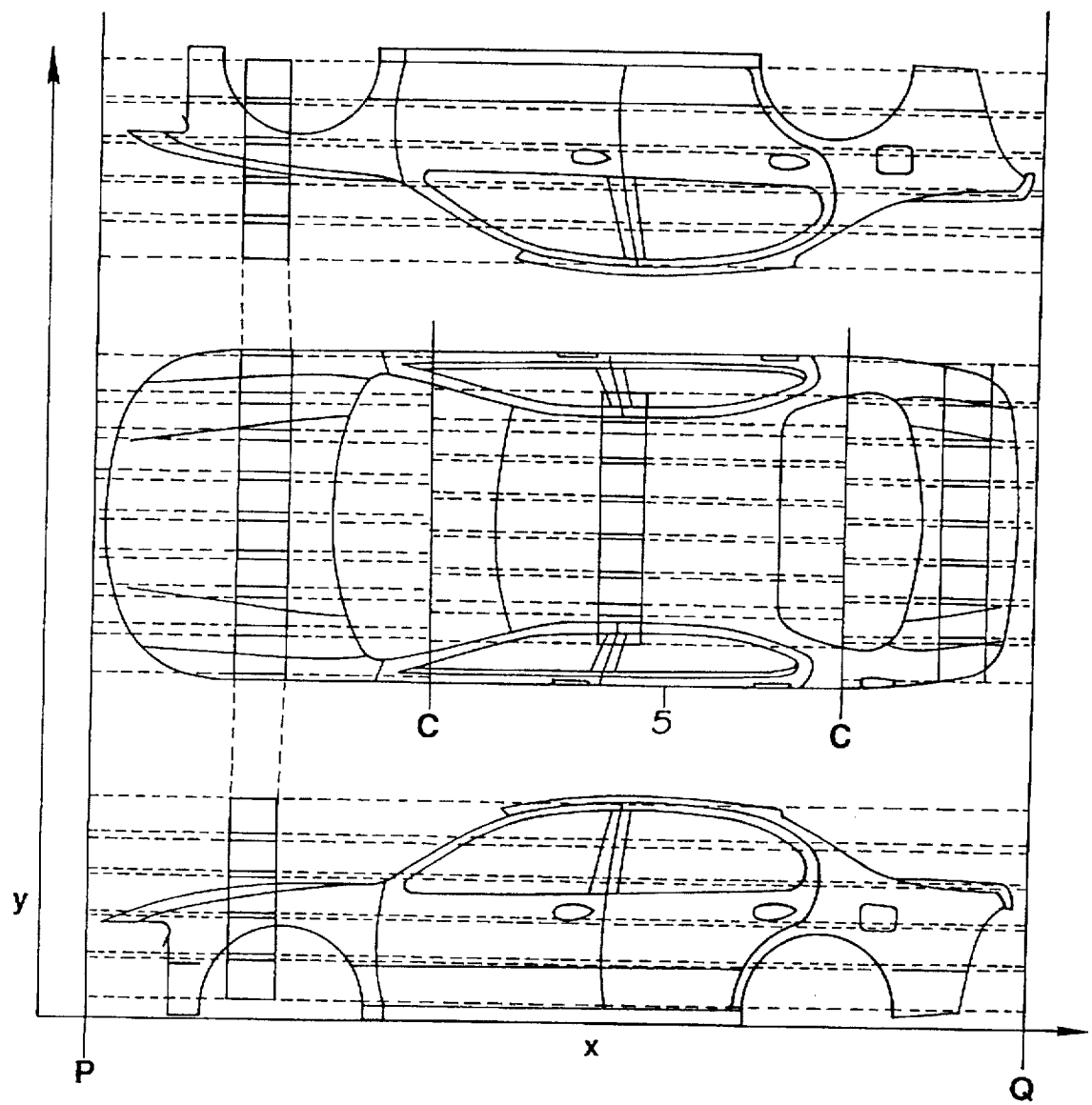
FIG. 21 is a development of the vehicle body.
Figure 22:
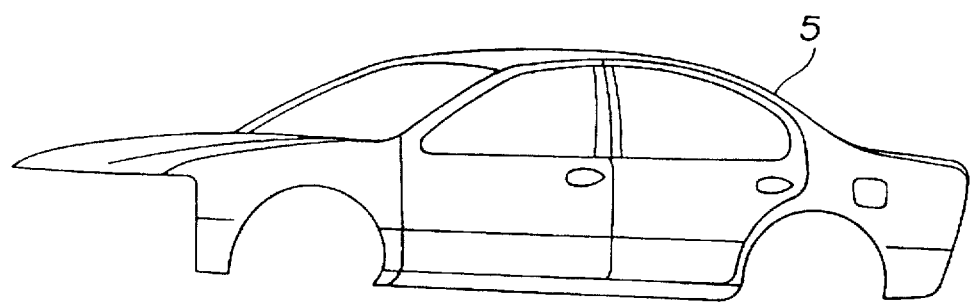
FIG. 22 shows a position to which the body is rotated.

The above sequence of steps are executed for the images produced in sequence from each of the CCD cameras 3 to calculate a defect position based on the defect list stored in the computer program. A mark is put to indicate the calculated defect position on the development of the vehicle body 5, as shown in FIG. 21. The defect position in the y-direction of FIG. 21 can be calculated based on the scale of the development of the vehicle body 5 since the position and size of the visual field of each of the Ccd cameras 3 are known and the y-direction coordinate of the gravity center of the white small image areas (defect) on the images is substantially unchanged. The defect position in the x direction of FIG. 21 with respect to the point P at which the surface defect inspection is initiated can be calculated based on the amount of movement of the vehicle body 5. The development having a mark at the defect position is outputted to an output unit such as a monitor, a printer or the like.

Figure 14:
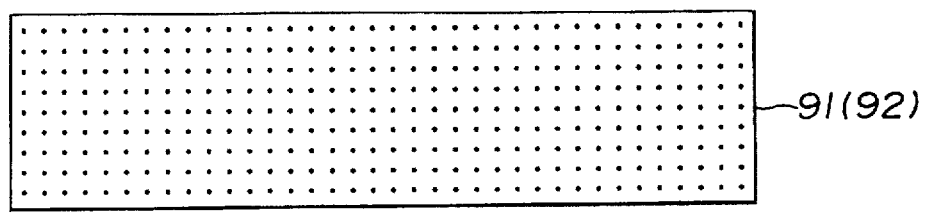
FIG. 14(a) shows a pattern formed on the surface of the reference model for camera visual field adjustment.
FIG. 14(b) shows a modified form of the pattern formed on the surface of the reference model for camera visual field adjustment.
Figure 14:
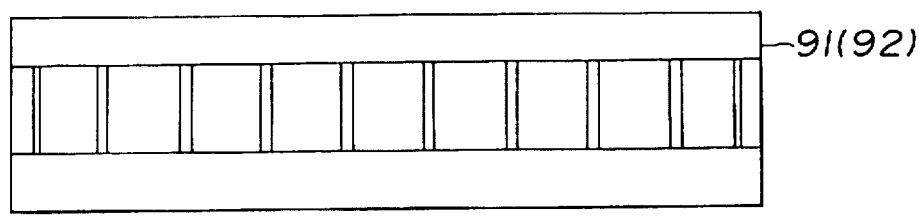

Preferably, two reference models are used for camera adjustment. The first reference model 91 is used to adjust the visual field, focus and visual field overlap of each of the CCD cameras for the defect inspection of the hood, trunk and door surfaces of the vehicle body 5. The second reference model 92 is used to adjust the visual field, focus and visual field overlap of each of the CCD cameras for the defect inspection of the roof and pillar surfaces of the vehicle body 5. FIG. 11(a) is an elevational view of the first reference model, 11(b) is a plan view of the first reference model, and 11(c) is a side view of the first reference model. FIG. 12(a) is an elevational view of the second reference model, 12(b) is a plan view of the second reference model, and 12(c) is a side view of the second reference model. The first and second reference models 91 and 92 have shapes substantially in conformity with the front contour of the vehicle body 5. In this embodiment, different groups of CCD cameras 3 are used when the hood surface of the vehicle body 5 is inspected than when the roof surface is inspected since there exists a great height difference between the hood and roof surfaces. For this reason, two kinds of reference models 91 and 92 are prepared. These reference models have shapes formed according to the configuration of the object (in the illustrated case vehicle body 5) under inspection. The first and second reference models 91 and 92 are formed on its surface with lattice lines drawn at uniform intervals. The operator can adjust the visual field of each of the CCD cameras 3, as shown in FIG. 10, while viewing the lattice lines displayed on a monitor. Alternatively, the first and second reference models 91 and 92 may be formed on its surface with dots arranged at uniform intervals, in place of the lattice lines, as shown in FIG. 14(a), or a square having substantially the same size as the visual field, as shown in FIG. 14(b). The operator can adjust the focus of each of the CCD cameras 3 while viewing the reference models 91 and 92 displayed on the monitor.

Figure 13:
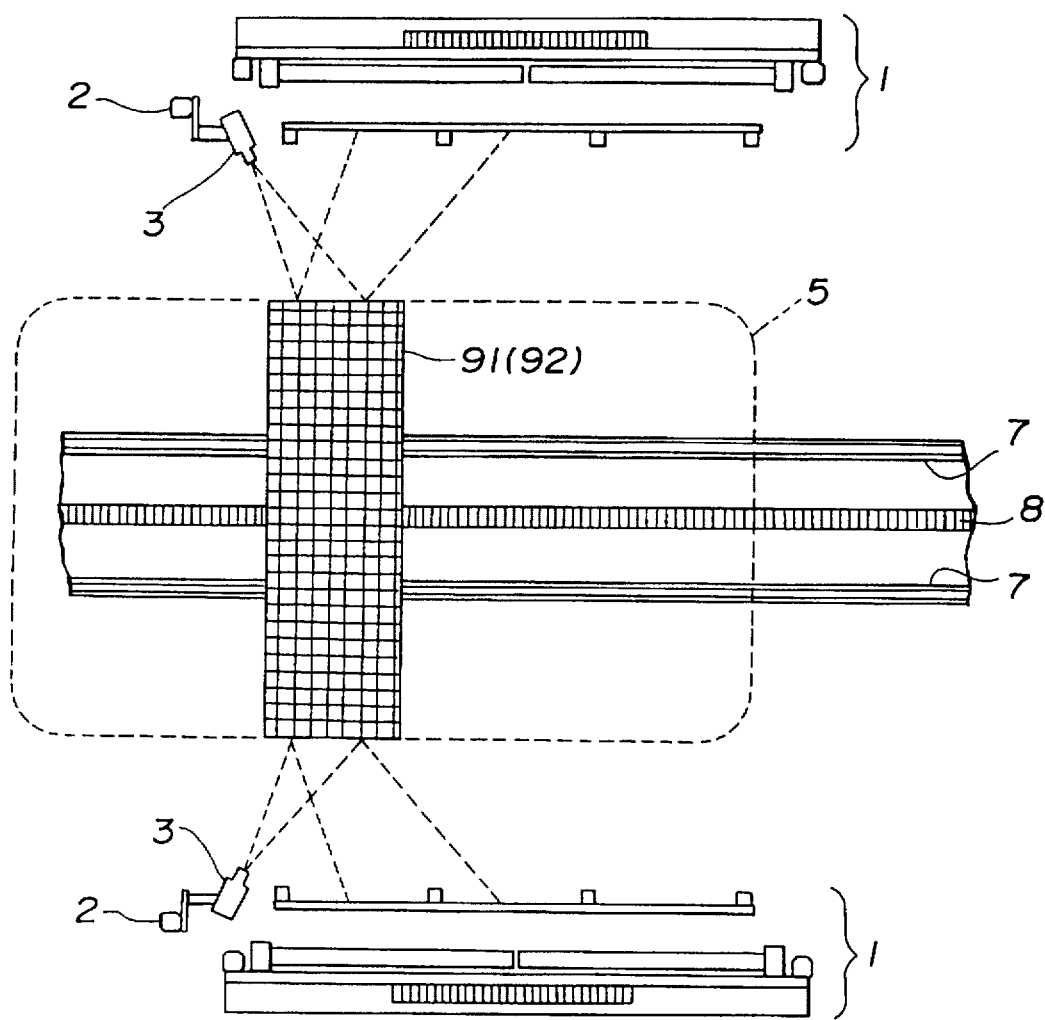
FIG. 13 is a plan view showing the positions of the lighting unit and cameras with respect to the reference model.
Figure 16:
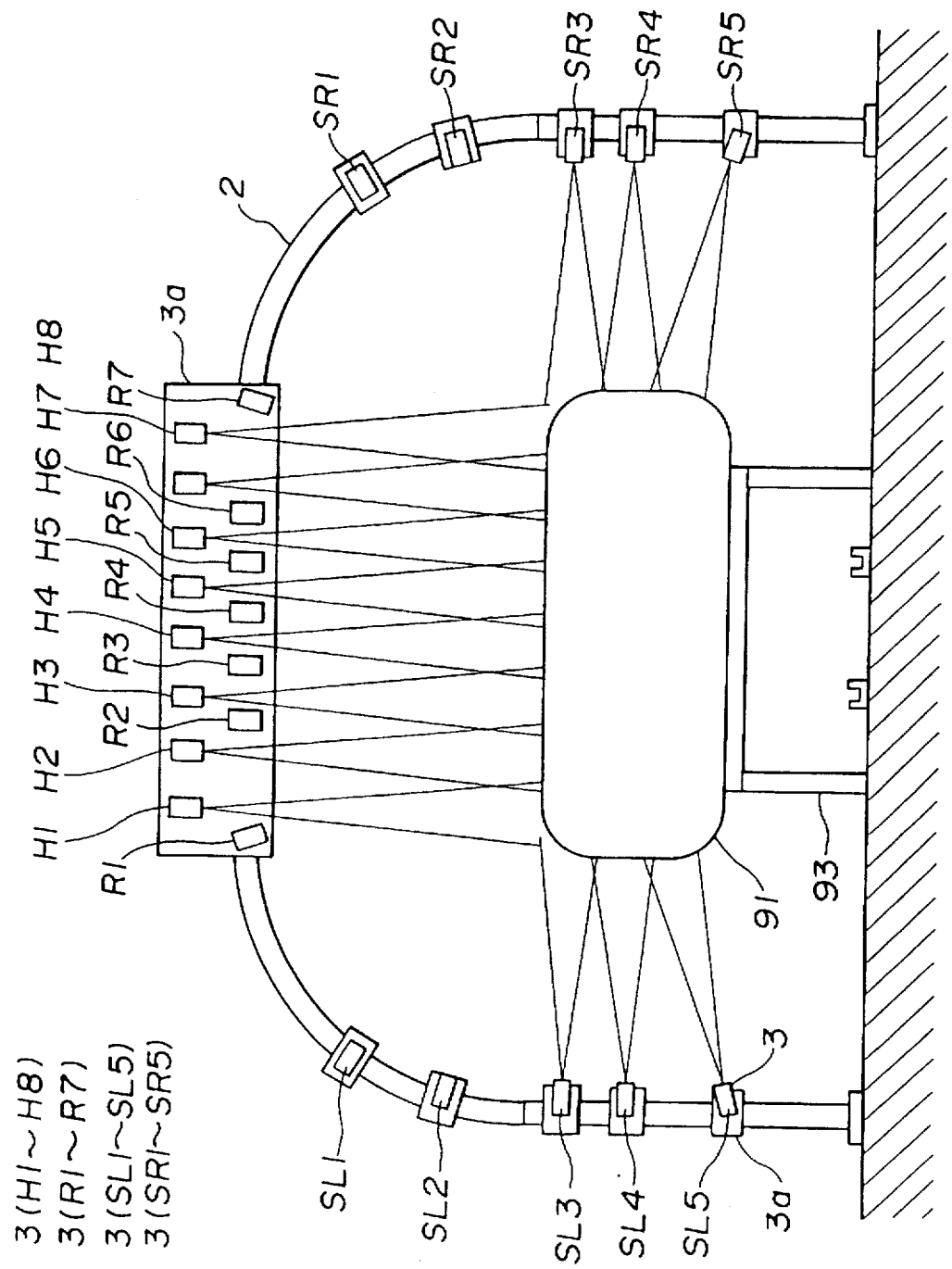
FIG. 16 is an elevational view showing the positions of the cameras with respect to one of the reference models.
Figure 17:
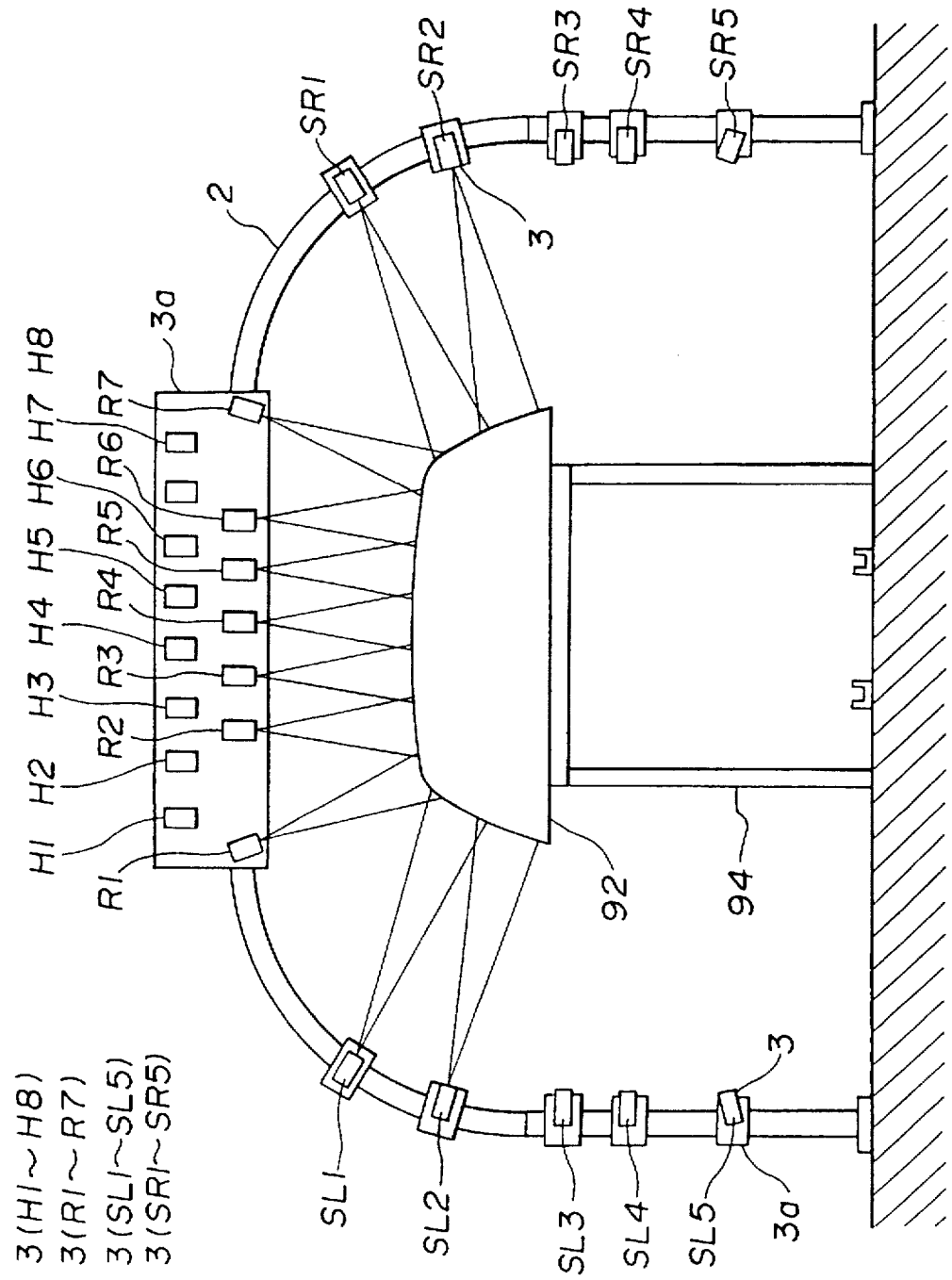
FIG. 17 is an elevational view showing the positions of the cameras with respect to the other reference model.

FIG. 13 shows the position of the first or second reference model 91 or 92 with respect to the lighting unit 1 and the CCD cameras 3 upon adjustment of the visual field and focus of each of the CCD cameras 3. Since the vehicle body 5 moves along the rails 7 by the function of the conveyor 8, the reference model 91 (92) is placed at the same position as when the vehicle body 5 is moved. In other words, the reference model is placed at an angle of 90 degrees with respect to the rails 7 with its opposite ends being in coincidence with the respective side surfaces of the vehicle body 5. FIG. 16 shows the position of the first reference model 91 with respect to the lighting unit 1 and the CCD cameras 3 upon camera adjustment for the defect inspection of the hood, trunk and door surfaces of the vehicle body 5. FIG. 17 shows the position of the second reference model 92 with respect to the lighting unit 1 and the CCD cameras 3 upon camera adjustment for the roof and pillar surfaces of the vehicle body 5. Each of the CCD cameras 3 is adjusted with the use of the first and second reference models 91 and 92 placed on tables 93 at positions held in coincidence with the position of the vehicle body 5.

Figure 11B:
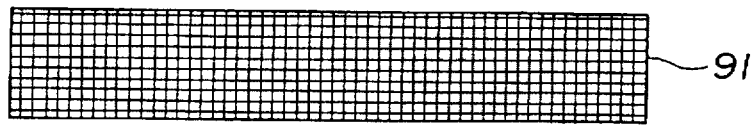
FIG. 11(b) is a plan view of the reference model used in adjusting the cameras for defect inspection on the hood, trunk and door surfaces of the vehicle body.
Figure 11A:
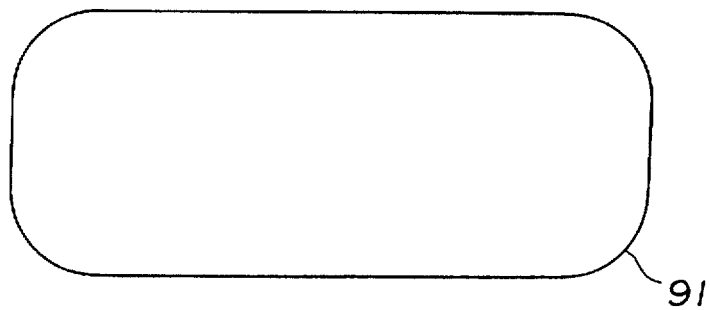
FIG. 11(a) is an elevational view of a reference model used in adjusting the cameras for defect inspection on the hood, trunk and door surfaces of the vehicle body.
Figure 11C:
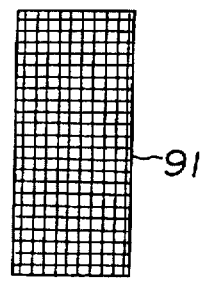
FIG. 11(c) is a side view of the reference model used in adjusting the cameras for defect inspection on the hood, trunk and door surfaces of the vehicle body.
Figure 12B:
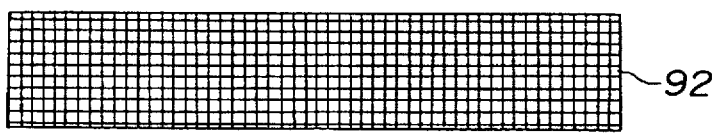
FIG. 12(b) is a plan view of the reference model used in adjusting the cameras for defect inspection on the roof and pillar surfaces of the vehicle body.
Figure 12A:
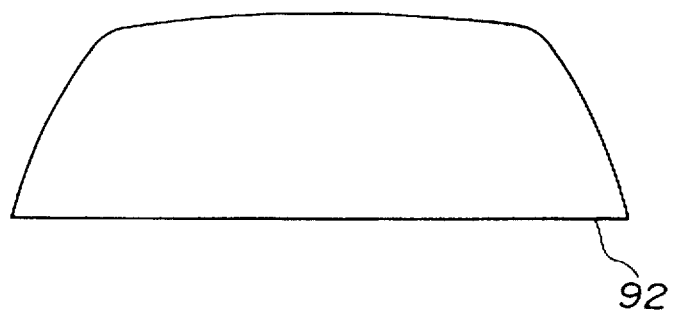
FIG. 12(a) is an elevational view of a reference model used in adjusting the cameras for defect inspection on the roof and pillar surfaces of the vehicle body.
Figure 12C:
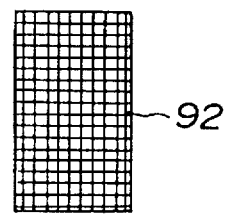
FIG. 12(c) is a side view of the reference model used in adjusting the cameras for defect inspection on the roof and pillar surfaces of the vehicle body.

As shown in FIGS. 11 and 12, the shapes of the first and second reference models 91 and 92 are substantially in conformity with the front contour of the vehicle body 5, that is, in conformity with the contour of the maximum transverse cross section, as viewed in the direction of transport of the vehicle body 5 so that the CCD cameras 3 are spaced at the shortest distance away from the reference models. If each of the CCD cameras 3 is adjusted to have an appropriate visual field under this condition, adjacent two CCD cameras 3 will have visual fields overlapping each other. If the overlap is adjusted when the contour is not at maximum, an appropriate overlap cannot be ensured at a position where the contour is greater than the contour used upon camera adjustment since the visual field decreases as the distance of the camera 3 from the surface of the vehicle body 5 decreases. It is, therefore, preferable that the reference models have a contour conforming to the greatest contour of the object under inspection.

Figure 15A:
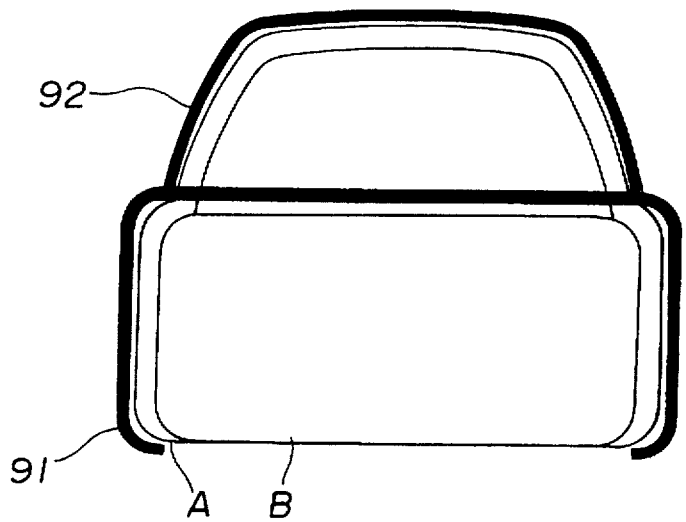
FIG. 15(a) is an elevational view used in explaining the shapes of the reference models prepared for one vehicle body shape.
Figure 15B:
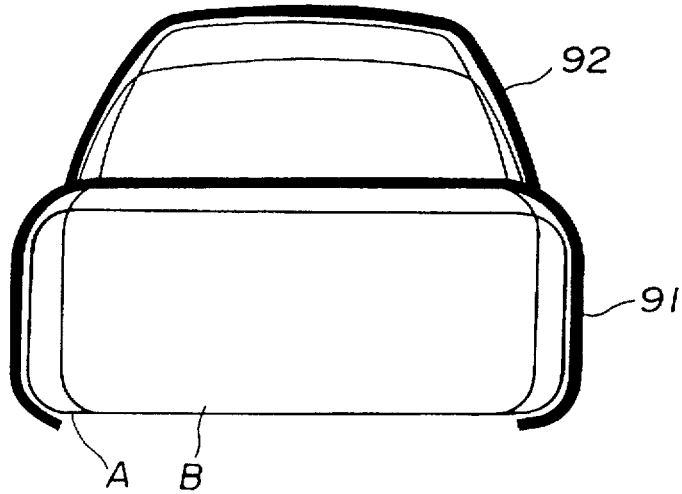
FIG. 15(b) is an elevational view used in explaining the shapes of the reference models prepared for another vehicle body shape.

FIG. 15(a) shows a vehicle having different body contours A and B where the body contour A is greater than the body contour B at all of the positions. In this case, the first and second reference models 91 and 92 have shapes substantially in conformity with the body contour A, as indicated by the bold lines of FIG. 15(a). FIG. 15(b) shows a vehicle having different body contours A and B where the body contour A is greater than the body contour B at some positions and is smaller than the body contour B at the other positions. In this case, the first and second reference models 91 and 92 have shapes substantially in conformity with the greater body contour, as indicated by the bold lines of FIG. 15(b).

The camera distance, that is, the distance of each of the CCD cameras 3 with respect to the painted surface of the vehicle body 5 under inspection changes according to the shape of the vehicle body 5. It is, therefore, required to take the focus in any case by setting the far limit at a great value sufficient for camera distance changes. Since the far limit depends on the lens aperture size, lens focal length and camera distance, a practical value of the lens aperture size can be calculated after the lens specifications, camera distance and far limit are determined based on the camera visual field size. The shutter speed of each of the CCD cameras 3 should be set at such a value that no image blur occurs due to the movement of the vehicle body 5. Thus, fine adjustment may be required for the lens aperture size and shutter speed according to the speed of movement of the vehicle body 5. The lens aperture size and shutter speed are adjusted in such a manner that the level of the signal outputted from each of the CCD cameras 3 cannot be saturated at the highest reflectivity of the light reflection characteristic of the painted surface of the vehicle body 5 with the use of an oscilloscope. Since the amount of the light reflected on the painted surface of the vehicle body 5 increases as the distance of the lighting unit 1 from the painted surface of the vehicle body 5 decreases and the distance of the CCD camera 3 from the painted surface of the vehicle body 5 decreases, adjustment may be made for the surface of the reference models 91 and 92 prepared to have shapes substantially in conformity with the maximum front contour of the vehicle body 5 since the lighting unit 1 and the CCD camera 3 are mounted at fixed positions. The CCD camera 3 is adjusted in such a manner that the level of the signal outputted from the CCD camera 3 is somewhat smaller than the white level in order to use the dynamic range in the direction of the brightness (luminance) with high efficiency. It is preferable to increase the camera adjustment efficiency by performing the camera visual field adjustment simultaneously in combination with the camera aperture size and shutter speed adjustment. This is possible if the background areas, except for the pattern used for camera visual field adjustment, of the surface of each of the first and second reference models 91 and 92 is painted in color having a high reflectivity such as white or silver metallic paint. If it is difficult to paint the adjustment surface of each of the reference models 91 and 92, the camera adjustments may be made with the use of a test piece placed in contact with the reference model. The test piece has a size greater than the visual field of the CCD camera 3 and painted in white or metallic silver.

If the image enhancement section 41 is designed to differentiate the signal fed from each of the CCD cameras 3 for edge detection, it will extract an image area having its luminance changed. Thus, the boundary lines of the bright and dark strip light patterns appear as white image areas, as shown in FIG. 19(b). If the defect indicative white small image area E appears at a position close to one of the boundary lines of the bright and dark strip light pattern, the it would appear as a unit with the one boundary line and would not appear as an isolate point. Furthermore, the surface defect inspection accuracy decreases since the frequency at which the defect indicative white small image area E disappears increases with an increase in the number of the boundary lines of the bright and dark strip light pattern on each of the images. The number of the boundary lines which appears on an image produced from a CCD camera 3 is greater when the CCD camera 3 is directed to a convex surface than when the CCD camera 3 is directed to a flat surface if the pitch of the brightness pattern is constant regardless of the position. For example, the front fender of the vehicle body 5 has a convex surface at its end. The convex surface acts as a convex mirror causing a greater number of boundary lines to appear on the image.

Figure 24:
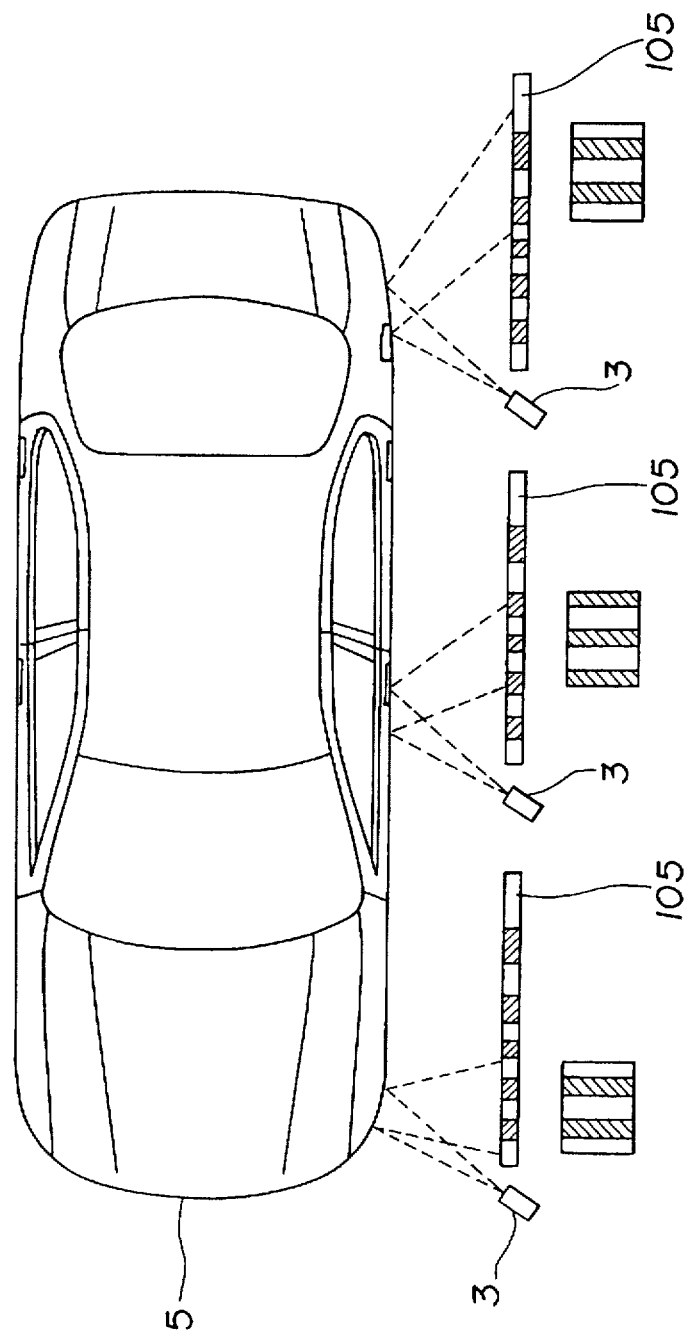
FIG. 24 is a plan view used in explaining the bright and dark strip light patterns for defect inspection at different positions on the surface of the vehicle body.
Figure 25:
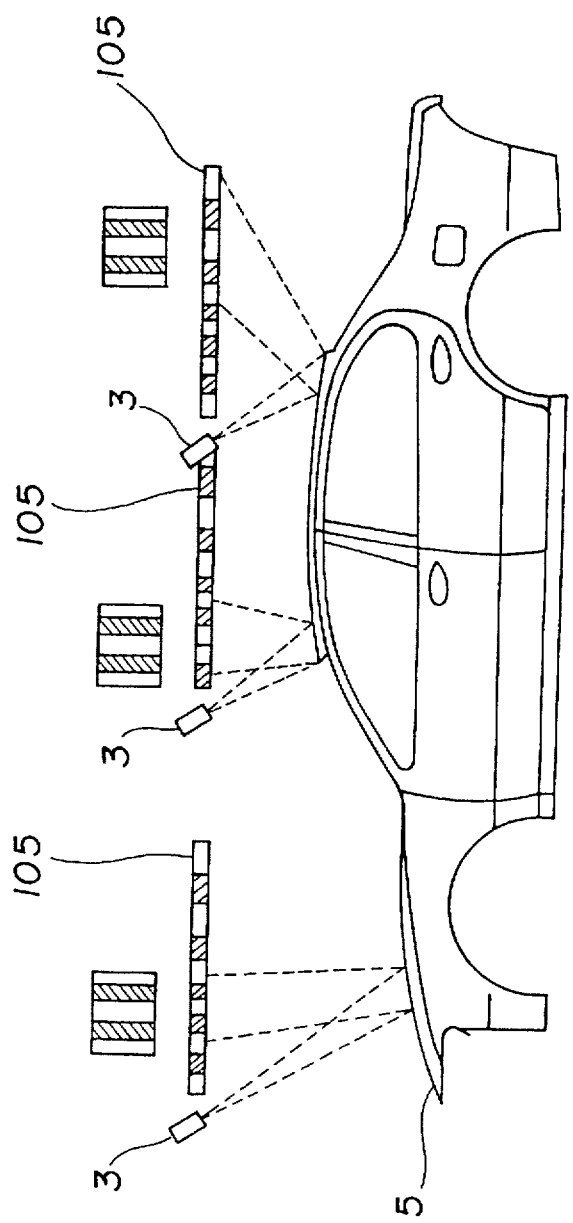
FIG. 25 is a side view used in explaining the bright and dark strip light patterns for defect inspection at different positions on the surface of the vehicle body.

Description will be made to one example of a solution for eliminating such a defect inspection accuracy reduction problem. In FIGS. 24 and 25, the broken lines indicate the bright and dark strip light pattern incident on the CCD camera 3 after it is projected through the light diffusion sheet 105 onto the painted surface of the vehicle body 5 and reflects from the vehicle body surfaces. For example, the bright and dark strip pattern may be designed to have such a pitch that four boundary lines appear on the image from the CCD camera 3 according to the configuration of the vehicle body 5. Although the number of the boundary lines of the bright and dark strip pattern is in question, the manner in which the bright and dark strip light pattern is produced on the image, that is, the order of the bright and dark image areas is not limited in any way since the order is not related to the principle utilizing diffused reflection on a defect. When the bright and dark strip light pattern has a pitch different when the CCD camera 3 is directed to the side surface of the vehicle body 5 than when the CCD camera 3 is directed to the horizontal surface thereof, as shown in FIGS. 24 and 25, the frosted black tapes may be stuck in such a manner that the bright and dark strip pattern is discontinuous at the round portions of the arched form of the light diffusion sheet 105 to prevent a great distortion of the bright and dark strip light pattern on the image in the round portions between the fender and hood surfaces of the vehicle body 5. Although four boundary lines are shown in FIGS. 24 and 25, it is to be understood, of course, that the number of the boundary lines is not limited in any way to four. Although the frequency at which a defect appears on the image increases as the number of the boundary lines decreases, the inspection accuracy for small defective areas will decrease if the pitch of the bright and dark strip pattern increases to such a great extent as to decrease the number of the boundary lines. This fact should be considered in designing the bright and dark strip pattern of the light diffusion sheet 105.

Figure 23:
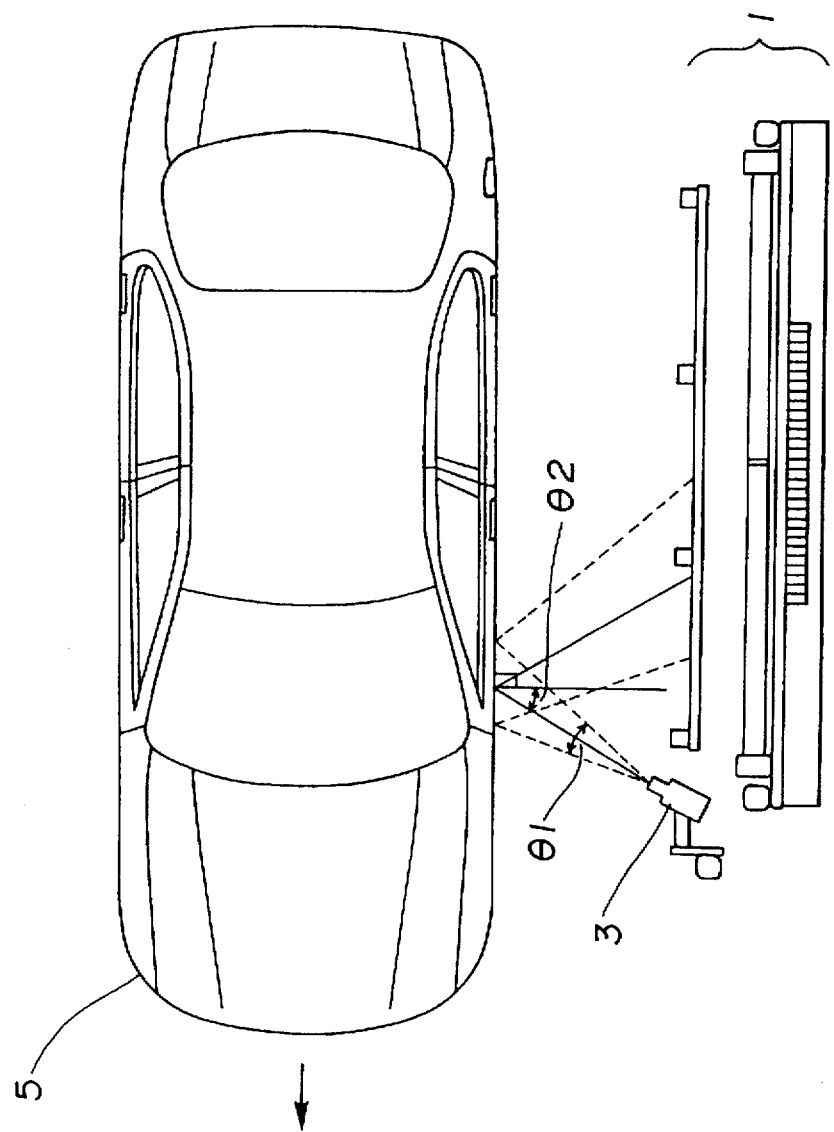
FIG. 23 is a plan view used in explaining the angle of view of a camera.

In this embodiment, the image produced from a CCD camera 3 includes a light and dark strip pattern of the light diffusion sheet 105 regardless of the configuration of the vehicle body 5 placed in the visual field of the CCD camera 3. In FIG. 23, the character θ1 is the angle of view of the CCD camera 3 and the character θ2 is the angle at which the CCD camera 3 is directed with respect to the direction normal to the direction of movement of the vehicle body 5. Sometimes, the position of the defect indicative mark put on the development of the vehicle body 5 of FIG. 21 may not be in coincidence with the actual position of the defect on the painted surface of the vehicle body 5 because of a difference between the visual point of the CCD camera 3 and the visual point of the development. That is, the CCD camera 3 is directed at an angle with respect to the direction of movement of the vehicle body 5, as shown in FIG. 23, whereas the development of the vehicle body 5 is viewed from a visual point positioned just beside the vehicle body 5 and just above the vehicle body 5. It is possible to eliminate this disagreement by produce the development of the vehicle body 5 as viewed from a visual point positioned at an angle with respect to the direction of movement of the vehicle body 5 like the CCD camera 3.

What is claimed is:

1. An apparatus for inspecting a defect on a surface of an object under inspection, comprising:

means for moving the object along a path;

a lighting unit shaped in an arched form laid across the path of movement of the object for illuminating the surface of the object;

light pattern forming means located between the lighting unit and the path of movement of the object for forming a bright and dark light pattern on the surface of the object;

a plurality of light sensors arranged in an arched form laid across the path of movement of the object, each of the light sensors producing an electrical signal in response to light of reflection from the surface of the object;

a processing unit for processing the electrical signal fed thereto from each of the light sensors for producing an image including the bright and dark light pattern; and means for inspecting a defect on the surface of the object based on the images fed thereto from the processing unit.

2. The surface defect inspection apparatus as claimed in claim 1, wherein the arched form of the lighting unit is shaped substantially in conformity with a contour of the object as viewed from the front in the direction of movement of the object.

3. The surface defect inspection apparatus as claimed in claim 2, further including a plurality of white background boards each of which has a plurality of light sources equally spaced from each other for diffused reflection of light from the light sources.

4. The surface defect inspection apparatus as claimed in claim 2, wherein the light pattern forming means includes a light diffusion sheet having transparent and frosted black portions arranged alternatively to form a bright and dark strip light pattern on the painted surface of the object.

5. The surface defect inspection apparatus as claimed in claim 4, wherein the light diffusion sheet spreads on a sheet guide shaped in an arched form laid across the path of movement of the object, the sheet guide being movable with respect to the light sources and the background boards.

6. The surface defect inspection apparatus as claimed in claim 5, wherein the light sensors are in the form of CCD cameras having a total strap visual field extending along the contour of the object as viewed from the front in the direction of movement of the object, adjacent two of the CCD cameras having visual fields partially overlapping each other.

7. The surface defect inspection apparatus as claimed in claim 6, wherein each of the images produced from the processing unit having a horizontal direction corresponding to the direction of movement of the object.

8. The surface defect inspection apparatus as claimed in claim 6, wherein each of the images produced from the processing unit having a vertical direction corresponding to the direction of movement of the object.

9. The surface defect inspection apparatus as claimed in claim 6, wherein the transparent and frosted black portions are arranged at a pitch determined based on the bright and dark light pattern on the image produced from each of the CCD cameras.

10. The surface defect inspection apparatus as claimed in claim 6, further including a reference model having a form substantially in conformity with the contour of the object as viewed from the front in the direction of movement of the object, the reference model being formed on its surface with a pattern of lines drawn at uniform intervals for adjustment of the visual field, focus and visual field overlap of each of the CCD cameras.

11. The surface defect inspection apparatus as claimed in claim 10, further including a test piece provided in contact with the reference model for adjustment of the lens aperture size and shutter speed of each of the CCD camera.

12. The surface defect inspection apparatus as claimed in claim 10, wherein the reference model having a form substantially in conformity with the contour of the greatest transverse cross section of the object.

13. The surface defect inspection apparatus as claimed in claim 12, further including a test piece provided in contact with the reference model for adjustment of the lens aperture size and shutter speed of each of the CCD camera.

14. The surface defect inspection apparatus as claimed in claim 12, wherein the reference model is painted in the same color as the brightest one of colors in which the surface of the object is painted for adjustment of the lens aperture size and shutter speed of each of the CCD camera.

15. The surface defect inspection apparatus as claimed in claim 14, further including a test piece provided in contact with the reference model for adjustment of the lens aperture size and shutter speed of each of the CCD camera.

16. The surface defect inspection apparatus as claimed in claim 6, further including a reference model having a form substantially in conformity with the contour of the object as viewed from the front in the direction of movement of the object, the reference model being formed on its surface with a pattern of dots arranged at uniform intervals for adjustment of the visual field, focus and visual field overlap of each of the CCD cameras.

17. The surface defect inspection apparatus as claimed in claim 16, further including a test piece provided in contact with the reference model for adjustment of the lens aperture size and shutter speed of each of the CCD camera.

18. The surface defect inspection apparatus as claimed in claim 1, further including a plurality of white background boards each of which has a plurality of light sources equally spaced from each other for diffused reflection of light from the light sources.

19. The surface defect inspection apparatus as claimed in claim 1, wherein the arched form in which the light sensors are arranged is shaped substantially in conformity with a contour of the object as viewed from the front in the direction of movement of the object.

20. The surface defect inspection apparatus as claimed in claim 1, wherein the light sensors are in the form of CCD cameras having a total strap visual field extending along a contour of the object as viewed from the front in the direction of movement of the object, adjacent two of the CCD cameras having visual fields partially overlapping each other.

21. The surface defect inspection apparatus as claimed in claim 20, wherein each of the images produced from the processing unit having a horizontal direction corresponding to the direction of movement of the object.

22. The surface defect inspection apparatus as claimed in claim 20, wherein each of the images produced from the processing unit having a vertical direction corresponding to the direction of movement of the object.

23. The surface defect inspection apparatus as claimed in claim 20, wherein the transparent and frosted black portions are arranged at a pitch determined based on the bright and dark light pattern on the image produced from each of the CCD cameras.

24. The surface defect inspection apparatus as claimed in claim 20, further including a reference model having a form substantially in conformity with the contour of the object as viewed from the front in the direction of movement of the object, the reference model being formed on its surface with a pattern of lines drawn at uniform intervals for adjustment of the visual field, focus and visual field overlap of each of the CCD cameras.

25. The surface defect inspection apparatus as claimed in claim 24, further including a test piece provided in contact with the reference model for adjustment of the lens aperture size and shutter speed of each of the CCD camera.

26. The surface defect inspection apparatus as claimed in claim 20, further including a reference model having a form substantially in conformity with the contour of the object as viewed from the front in the direction of movement of the object, the reference model being formed on its surface with a pattern of dots arranged at uniform intervals for adjustment of the visual field, focus and visual field overlap of each of the CCD cameras.

27. The surface defect inspection apparatus as claimed in claim 26, further including a test piece provided in contact with the reference model for adjustment of the lens aperture size and shutter speed of each of the CCD camera.

28. The surface defect inspection apparatus as claimed in claim 26, wherein the reference model having a form substantially in conformity with the contour of the greatest transverse cross section of the object.

29. The surface defect inspection apparatus as claimed in claim 28, further including a test piece provided in contact with the reference model for adjustment of the lens aperture size and Shutter speed of each of the CCD camera.

30. The surface defect inspection apparatus as claimed in claim 28, wherein the reference model is painted in the same color as the brightest one of colors in which the surface of the object is painted for adjustment of the lens aperture size and shutter speed of each of the CCD camera.

31. The surface defect inspection apparatus as claimed in claim 30, further including a test piece provided in contact with the reference model for adjustment of the lens aperture size and shutter speed of each of the CCD camera.

32. The surface defect inspection apparatus as claimed in claim 1, wherein the defect inspecting means includes means for extracting spatial frequency components having a frequency higher than a predetermined value and a level greater than a predetermined value from the images produced based on the electrical signals fed from the light sensors to produce an enhanced image, and means for detecting an image portion moving in a specified direction and at a specified speed from the enhanced images produced in sequence.

33. The surface defect inspection apparatus as claimed in claim 32, wherein the detect inspecting means includes means for detecting initiation and termination of the surface defect inspection, means for measuring an amount of movement of the object after the detected initiation of the surface defect inspection, means for calculating a position of the detected image portion on the surface of the object, and means for indicating the calculated position on a development of the object.

34. The surface defect inspection apparatus as claimed in claim 33, wherein the development of the object is drawn according to an angle of view of each of the light sensors with respect to the object and an angle at which each of the light sensors is directed with respect to the object.

* * * * *